US009993564B2

(12) United States Patent
Freskgard et al.

(10) Patent No.: US 9,993,564 B2
(45) Date of Patent: Jun. 12, 2018

(54) BLOOD BRAIN BARRIER SHUTTLE

(71) Applicant: Hoffmann-La Roche Inc., Little Falls, NJ (US)

(72) Inventors: Per-Ola Freskgard, Reinach (CH); Roland Schmucki, Basel (CH); Eduard Urich, Loerrach (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days. days.

(21) Appl. No.: 15/240,768

(22) Filed: Aug. 18, 2016

(65) Prior Publication Data

US 2017/0128581 A1 May 11, 2017

Related U.S. Application Data

(63) Continuation of application No. PCT/EP2015/053244, filed on Feb. 17, 2015.

(30) Foreign Application Priority Data

Feb. 19, 2014 (EP) .................................... 14155687

(51) Int. Cl.
*A61K 47/50* (2017.01)
*A61K 47/48* (2006.01)
*C07K 16/18* (2006.01)
*C07K 16/28* (2006.01)
*A61K 38/04* (2006.01)
*A61K 47/64* (2017.01)

(52) U.S. Cl.
CPC ........ *A61K 47/48246* (2013.01); *C07K 16/18* (2013.01); *C07K 16/28* (2013.01); *A61K 38/04* (2013.01); *A61K 47/50* (2017.08); *A61K 47/64* (2017.08)

(58) Field of Classification Search
CPC .. A61K 47/48246; A61K 47/50; A61K 47/64; A61K 38/04; C07K 16/18; C07K 16/28; C07K 5/08
See application file for complete search history.

(56) References Cited

U.S. PATENT DOCUMENTS

| | | | |
|---|---|---|---|
| 7,557,182 B2 * | 7/2009 | Beliveau | A61K 47/48246 424/570 |
| 2003/0104993 A1 | 6/2003 | Rueger | |
| 2004/0191265 A1 | 9/2004 | Schenerman | |
| 2005/0187147 A1 | 8/2005 | Newman | |
| 2006/0039929 A1 | 2/2006 | Fernandez-Salas | |
| 2011/0003750 A1 | 1/2011 | Tregear | |
| 2012/0141416 A1 * | 6/2012 | Demeule | A61K 47/48246 424/85.7 |
| 2014/0024597 A1 * | 1/2014 | Troy | A61K 38/55 514/17.7 |

FOREIGN PATENT DOCUMENTS

| | | |
|---|---|---|
| CN | 101497651 A | 8/2009 |
| FR | 2 944 020 A1 | 10/2010 |
| WO | 02/20822 A2 | 3/2002 |
| WO | 2007/120648 A2 | 10/2007 |
| WO | 2010/121023 A2 | 10/2010 |
| WO | 2011/046938 A2 | 4/2011 |
| WO | 2011/091304 A1 | 7/2011 |
| WO | 2013/041238 A1 | 3/2013 |

OTHER PUBLICATIONS

Bastit, A. et al., Novasep presentation. Retrieved from internet on Aug. 11, 2016: biotuesday.fr/files/2010/09/novasep.pdf.
Gonzalez et al., "Targeting choroid plexus epithelia and ventricular ependyma for drug delivery to the central nervous system" BMC NEUROSCI 12(4): 1-12 (2011).
Pasqualini et al., "Aminopeptidase N is a receptor for tumor-homing peptides and a target for inhibiting angiogenesis" CANCER RES 60:722-727 (Feb. 1, 2000).
Rousselle et al., "Enhanced Delivery of Doxorubiein into the Brain via a Peptide-Vector-Mediated Strategy: Saturation Kinetics and Specificity" J PHARMACOL EXP THER 296(1): 124-131 (2001).
Smith et al., "Peptide sequences mediating tropism to intact blood-brain barrier: An in vivo biodistribution study using phage display" Peptides 38(1):172-180 (2012).

* cited by examiner

*Primary Examiner* — Kimberly Ballard

(57) ABSTRACT

A blood brain barrier shuttle comprising a brain effector entity and a brain targeting peptide.

12 Claims, 8 Drawing Sheets

SEQUENCE LISTING

```
<160> NUMBER OF SEQ ID NOS: 47

<210> SEQ ID NO 1
<211> LENGTH: 14
<212> TYPE: PRT
<213> ORGANISM: Artificial Sequence
<220> FEATURE:
<223> OTHER INFORMATION: Brain targeting peptide

<400> SEQUENCE: 1

Leu Tyr Val Leu His Ser Arg Gly Leu Trp Gly Phe Lys Leu
1               5                   10

<210> SEQ ID NO 2
<211> LENGTH: 5
<212> TYPE: PRT
<213> ORGANISM: Artificial Sequence
<220> FEATURE:
<223> OTHER INFORMATION: Brain targeting peptide
```

```
<400> SEQUENCE: 2

Leu Gly Ser Val Ser
1               5

<210> SEQ ID NO 3
<211> LENGTH: 11
<212> TYPE: PRT
<213> ORGANISM: Artificial Sequence
<220> FEATURE:
<223> OTHER INFORMATION: Brain targeting peptide

<400> SEQUENCE: 3

Gly Phe Val Arg Phe Arg Leu Ser Asn Thr Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 4

Lys Val Ala Trp Arg Val Phe Ser Leu Phe Trp Lys
1               5                   10

<210> SEQ ID NO 5
<211> LENGTH: 5
<212> TYPE: PRT
<213> ORGANISM: Artificial Sequence
<220> FEATURE:
<223> OTHER INFORMATION: Brain targeting peptide

<400> SEQUENCE: 5

Ser Val His Gly Val
1               5

<210> SEQ ID NO 6
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 6

Gly Arg Pro Gln Lys Ile Asn Gly Ala Arg Val Cys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 7

Met Arg Trp Phe Phe Ser His Ala Ser Gln Gly Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Brain targeting peptide
```

```
<400> SEQUENCE: 8

Arg Leu Ser Ser Val Asp Ser Asp Leu Ser Gly Cys
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Brain targeting peptide

<400> SEQUENCE: 9

Ile Gly Thr Leu Thr Thr
1               5

<210> SEQ ID NO 10
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 10

Tyr Asn Gln Ser Leu Leu Gln Gly Tyr Arg Tyr Trp
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 11

Arg Ser Thr Ala Ser Thr Ser Tyr Pro Phe Phe Phe
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 12

Ile Ser Asn Arg Ser His Lys Gly Leu Met Val Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 13

Asp Ala Ala Glu Ser Val Leu Val Gly Thr Val Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Brain targeting peptide
```

```
<400> SEQUENCE: 14

Tyr Ala Trp Gly Gly Gly Trp Val Leu Gln Trp Phe
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Brain targeting peptide

<400> SEQUENCE: 15

Tyr Ser Met Val Phe Val Gly Ile Lys Leu
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Brain targeting peptide

<400> SEQUENCE: 16

Asp Val Ala Lys Val Ser
1               5

<210> SEQ ID NO 17
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 17

Arg Arg Pro Ala Pro Leu Ile Met Phe Arg Met Ile
1               5                   10

<210> SEQ ID NO 18
<211> LENGTH: 19
<212> TYPE: PRT
<213> ORGANISM: Artificial Sequence
<220> FEATURE:
<223> OTHER INFORMATION: Brain targeting peptide

<400> SEQUENCE: 18

Asp Pro Gln Ile Leu Met Gly Val Leu Arg Ser Ile Arg Gly Phe Gly
1               5                   10                  15

Val Lys Leu

<210> SEQ ID NO 19
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 19

Ser Arg Tyr Ser Ile Gly Gly Asn Asn Gly Val Thr
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Brain targeting peptide
```

```
<400> SEQUENCE: 20

Ser Gly Ser Gly Ile Gly Leu Asp Arg Trp Arg Val
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Brain targeting peptide

<400> SEQUENCE: 21

Trp Gly Cys Asn Gly Thr Glu Trp Arg Gly Leu Leu Gly Ile Lys Leu
1               5                   10                  15

<210> SEQ ID NO 22
<211> LENGTH: 7
<212> TYPE: PRT
<213> ORGANISM: Artificial Sequence
<220> FEATURE:
<223> OTHER INFORMATION: Brain targeting peptide

<400> SEQUENCE: 22

Asn Ser His Ala Met Ser Cys
1               5

<210> SEQ ID NO 23
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 23

Ser Thr Val Val Cys Phe Lys Gly Val Pro Thr Gly
1               5                   10

<210> SEQ ID NO 24
<211> LENGTH: 7
<212> TYPE: PRT
<213> ORGANISM: Artificial Sequence
<220> FEATURE:
<223> OTHER INFORMATION: Brain targeting peptide

<400> SEQUENCE: 24

Thr Trp Leu Phe Ser Leu Gly
1               5

<210> SEQ ID NO 25
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 25

Leu Pro Gly Gly Ser Pro Gly His Ile Leu Val Cys
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Brain targeting peptide
```

```
<400> SEQUENCE: 26

Gly Trp Ile Pro Tyr Asp Gly Gly Asn Arg Ala Arg
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Brain targeting peptide

<400> SEQUENCE: 27

Ser Thr Met Arg Tyr Val Gly Val Thr Cys Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 28

Gly Cys Ala Ser Pro Ala Ser Thr Ser Phe His Ser
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Brain targeting peptide

<400> SEQUENCE: 29

Leu Arg Pro Arg Gly Ala Phe Gln Arg Arg Asp Phe Lys Leu
1               5                   10

<210> SEQ ID NO 30
<211> LENGTH: 5
<212> TYPE: PRT
<213> ORGANISM: Artificial Sequence
<220> FEATURE:
<223> OTHER INFORMATION: Brain targeting peptide

<400> SEQUENCE: 30

Glu Leu Val His Ala
1               5

<210> SEQ ID NO 31
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 31

Phe Leu Ile Gln Trp Gly Ala Val Leu Ser Arg Gly
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Brain targeting peptide
```

<400> SEQUENCE: 32

Val Arg Asp Trp Ala Tyr Val Tyr Ser Thr Val Leu
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 33

Thr Ala Val Phe Ser Ala Leu Ser Met Leu Arg Gly
1               5                   10

<210> SEQ ID NO 34
<211> LENGTH: 4
<212> TYPE: PRT
<213> ORGANISM: Artificial Sequence
<220> FEATURE:
<223> OTHER INFORMATION: Brain targeting peptide

<400> SEQUENCE: 34

Ala Val Glu Ser
1

<210> SEQ ID NO 35
<211> LENGTH: 8
<212> TYPE: PRT
<213> ORGANISM: Artificial Sequence
<220> FEATURE:
<223> OTHER INFORMATION: Brain targeting peptide

<400> SEQUENCE: 35

Arg Pro Arg Ala Gln Gly Ala Leu
1               5

<210> SEQ ID NO 36
<211> LENGTH: 12
<212> TYPE: PRT
<213> ORGANISM: Artificial Sequence
<220> FEATURE:
<223> OTHER INFORMATION: Brain targeting peptide

<400> SEQUENCE: 36

Leu Trp Val Ser Val Pro Arg Ala Arg Ile Ile Gln
1               5                   10

<210> SEQ ID NO 37
<211> LENGTH: 67
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (16)..(61)
<223> OTHER INFORMATION: n  is a, c, g or t; h is a or c

<400> SEQUENCE: 37
ggggatccga attctnhhnh hnhhnhhnhh nhhnhhnhhn hhnhhnhhnh htaagcttgc      60
ggccgca                                                               67

```
<210> SEQ ID NO 38
<211> LENGTH: 14
<212> TYPE: DNA
<213> ORGANISM: Artificial Sequence
<220> FEATURE:
<223> OTHER INFORMATION: PCR Primer

<400> SEQUENCE: 38
tcgaacgccg gcgt                                                       14

<210> SEQ ID NO 39
<211> LENGTH: 50
<212> TYPE: DNA
<213> ORGANISM: Artificial Sequence
<220> FEATURE:
<223> OTHER INFORMATION: PCR Primer

<400> SEQUENCE: 39
ccatctcatc cctgcgtgtc tccgactcag ggagctgtcg tattccagtc                 50

<210> SEQ ID NO 40
<211> LENGTH: 50
<212> TYPE: DNA
<213> ORGANISM: Artificial Sequence
<220> FEATURE:
<223> OTHER INFORMATION: PCR Primer

<400> SEQUENCE: 40
cctatcccct gtgtgccttg gcagtctcag aacccctcaa gacccgttta                 50

<210> SEQ ID NO 41
<211> LENGTH: 18
<212> TYPE: DNA
<213> ORGANISM: Artificial Sequence
<220> FEATURE:
<223> OTHER INFORMATION: PCR Primer

<400> SEQUENCE: 41
agtacgcaat gggccacg                                                   18

<210> SEQ ID NO 42
<211> LENGTH: 19
<212> TYPE: DNA
<213> ORGANISM: Artificial Sequence
<220> FEATURE:
<223> OTHER INFORMATION: PCR Primer

<400> SEQUENCE: 42
gagcgcatat agttcctcc                                                  19

<210> SEQ ID NO 43
<211> LENGTH: 18
<212> TYPE: DNA
<213> ORGANISM: Artificial Sequence
<220> FEATURE:
<223> OTHER INFORMATION: PCR Primer

<400> SEQUENCE: 43
caggagctgt cgtattcc                                                   18

<210> SEQ ID NO 44
<211> LENGTH: 19
<212> TYPE: DNA
<213> ORGANISM: Artificial Sequence
<220> FEATURE:
<223> OTHER INFORMATION: Sequencing Primer
```

```
                                          -continued

<400> SEQUENCE: 44
aaaaacccct caagacccg                                                        19

<210> SEQ ID NO 45
<211> LENGTH: 21
<212> TYPE: DNA
<213> ORGANISM: Artificial Sequence
<220> FEATURE:
<223> OTHER INFORMATION: Start insert

<400> SEQUENCE: 45
gtgatgctcg gggatccgaa t                                                     21

<210> SEQ ID NO 46
<211> LENGTH: 24
<212> TYPE: DNA
<213> ORGANISM: Artificial Sequence
<220> FEATURE:
<223> OTHER INFORMATION: Stop insert

<400> SEQUENCE: 46
taagcttgcg gccgcactcg agta                                                  24

<210> SEQ ID NO 47
<211> LENGTH: 30
<212> TYPE: DNA
<213> ORGANISM: Artificial Sequence
<220> FEATURE:
<223> OTHER INFORMATION: Background insert

<400> SEQUENCE: 47
cctgcaggga tatcccggga gctcgtcgac                                            30
```

BLOOD BRAIN BARRIER SHUTTLE

CROSS REFERENCE TO RELATED APPLICATIONS

This application is a continuation of International Application No. PCT/EP2015/053244, having an international filing date of Feb. 17, 2015, the entire contents of which are incorporated herein by reference, and which claims benefit to European Application No. 14155687.8, filed Feb. 19, 2014.

SEQUENCE LISTING

This application hereby incorporates by reference the material of the electronic Sequence Listing filed concurrently herewith. The material in the electronic Sequence Listing is submitted as a text (.txt) file entitled "P31897-US_Sequence_Listing_ST25" created on Aug. 10, 2016, which has a file size of 10 kilo bytes, and is herein incorporated by reference in its entirety.

FIELD OF THE INVENTION

The present invention concerns the fields of molecular medicine and targeted delivery of therapeutic or diagnostic agents. More specifically, the present invention relates to peptides that target the cerebrospinal fluid (CSF) and the brain of an organism.

BACKGROUND

Brain penetration and/or CSF penetration of neurological disorder drugs such as e.g. large biotherapeutic drugs or small molecule drugs having a low brain penetration, is strictly limited by the extensive and impermeable blood-brain barrier (BBB) or blood-CSF barrier (BCSFB) together with the other cell component of the neurovascular unit (NVU). Many strategies to overcome this obstacle have been tested and one is to utilize transcytosis pathways mediated by endogenous receptors expressed on the brain capillary endothelium. Recombinant proteins such as monoclonal antibodies or peptides have been designed against these receptors to enable receptor-mediated delivery of biotherapeutics and diagnostics to the brain. However, strategies to maximize brain uptake while minimizing misssorting within the brain endothelial cells (BECs), and the extent of accumulation within certain organelles (especially organelles that lead to degradation of the biotherapeutic) in BECs, remain unexplored.

Monoclonal antibodies and other biotherapeutics have huge therapeutic potential for treatment of pathology in the central nervous system (CNS). However, their route into the brain is prevented by the BBB. Previous studies have illustrated that a very small percentage (approximately 0.1%) of an IgG injected in the bloodstream are able to penetrate into the CNS compartment (Felgenhauer, Klin. Wschr. 52: 1158-1164 (1974)). This will certainly limit any pharmacological effect due to the low concentration of the antibody within the CNS. The cerebrospinal fluid (CSF) is in direct contact with the neurons in the CNS.

Therefore, there is a need for delivery systems of neurological disorder drugs that target the brain of an organism.

SUMMARY OF THE INVENTION

In a first aspect the present invention provides a blood brain barrier shuttle comprising a brain effector entity and a brain targeting peptide comprising a three amino acid peptide motif selected from the group consisting of: Phe-Lys-Leu (FKL), Arg-Gly-Leu (RGL), Ser-Arg-Gly (SRG), Tyr-Val-Leu (YVL), Trp-Gly-Phe (WGF), Val-Leu-His (VLH), Leu-Tyr-Val (LYV), Leu-Trp-Gly (LWG), Leu-His-Ser (LHS), His-Ser-Arg (HSR), Gly-Leu-Trp (GLW), Gly-Phe-Lys (GFK), Arg-Leu-Ser (RLS), Gly-Ser-Val (GSV), Ser-Val-Ser (SVS), Leu-Gly-Ser (LGS), Val-Arg-Phe (VRF), Ser-Asn-Thr (SNT), Arg-Phe-Arg (RFR), Asn-Thr-Arg (NTR), Leu-Ser-Asn (LSN), Gly-Phe-Val (GFV), Phe-Val-Arg (FVR), Phe-Arg-Leu (FRL), Trp-Arg-Val (WRV), Phe-Ser-Leu (FSL), Val-Phe-Ser (VFS), Val-Ala-Trp (VAW), Ser-Leu-Phe (SLF), Arg-Val-Phe (RVF), Leu-Phe-Trp (LFW), Lys-Val-Ala (KVA), Phe-Trp-Lys (FWK), Ala-Trp-Arg (AWR), Val-His-Gly (VHG), Ser-Val-His (SVH), His-Gly-Val (HGV), Arg-Val-Cys (RVC), Arg-Pro-Gln (RPQ), Gln-Lys-Ile (QKI), Pro-Gln-Lys (PQK), Asn-Gly-Ala (NGA), Lys-Ile-Asn (KIN), Ile-Asn-Gly (ING), Gly-Arg-Pro (GRP), Gly-Ala-Arg (GAR), Ala-Arg-Val (ARV), Leu-Ser-Gly (LSG), Val-Asp-Ser (VDS), and Ser-Val-Asp (SVD).

In a particular embodiment of the blood brain barrier shuttle, the brain targeting peptide comprising a three amino acid peptide motif comprises between 1-25 three amino acid peptide motifs, in particular 1-15, more particularly 1-10, even more particularly 1-5 three amino acid peptide motifs.

In a particular embodiment of the blood brain barrier shuttle, the brain shuttle comprises the brain effector entity, a linker and the brain targeting peptide comprising a three amino acid peptide motif, wherein the linker couples the effector entity to the brain targeting peptide comprising a three amino acid peptide motif.

In a particular embodiment of the blood brain barrier shuttle, the brain targeting peptide comprising a three amino acid peptide motif is selected from the group consisting of SEQ. ID. NOs. 1 to 36, preferably SEQ. ID. NOs. 1, 6 and 8.

In a particular embodiment of the blood brain barrier shuttle, the brain effector entity is selected from the group consisting of neurological disorder drugs, neurotrophic factors, growth factors, enzymes, cytotoxic agents, antibodies directed to a brain target, monoclonal antibodies directed to a brain target, peptides directed to a brain target.

In a particular embodiment of the blood brain barrier shuttle, the brain target is selected from the group consisting of β-secretase 1, Aβ, epidermal growth factor, epidermal growth factor receptor 2, Tau, phosphorylated Tau, apolipoprotein E4, alpha synuclein, oligomeric fragments of alpha synuclein, CD20, huntingtin, prion protein, leucine rich repeat kinase 2, parkin, presenilin 2, gamma secretase, death receptor 6, amyloid precursor protein, p75 neurotrophin receptor, and caspase 6.

In a particular embodiment of the blood brain barrier shuttle, the brain effector entity is selected from the group consisting of proteins, polypeptides, and peptides.

In a particular embodiment of the blood brain barrier shuttle, the brain effector entity comprises a full length antibody directed to a brain target, preferably a full length IgG.

In a particular embodiment of the blood brain barrier shuttle, the effector entity is a full length antibody directed to Aβ.

In a particular embodiment of the blood brain barrier shuttle, the effector entity is a full length antibody directed to phosphorylated Tau.

In a particular embodiment of the blood brain barrier shuttle, the effector entity is a full length antibody directed to alpha synuclein.

In a second aspect, the present invention provides a pharmaceutical formulation comprising the blood brain barrier shuttle of the present invention and a pharmaceutical carrier.

Furthermore, the present invention provides the use of the brain shuttle as a medicament, in particular the use of the brain shuttle for the treatment of a neurodegenerative disorder, in particular Alzheimer's disease and for the treatment of a neuroinflammatory disorder in particular Multiple Sclerosis.

Aspects of the invention include a BBB shuttle comprising a brain targeting peptide that is covalently coupled to the agent to be delivered. The agent may be a drug, a chemotherapeutic agent, a radioisotope, a pro-apoptosis agent, an anti-angiogenic agent, a hormone, an enzyme, a cytokine, a growth factor, a cytotoxic agent, a peptide, a protein, an antibiotic, an antibody, a Fab fragment of an antibody, a smaller fragment of an antibody, an imaging agent, survival factor, an anti-apoptotic agent, a hormone antagonist or an antigen. In a further aspect of the invention, an anti-angiogenic agent may be selected from the group consisting of thrombospondin, angio-statin 5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-B, thrombospondin, 2-methoxyoestradiol, proliferin-related protein, carboxiamidotriazole, CMI 01, Manmastat, pentosan polysuiphate, angiopoietin 2 (Regeneron), interferon-alpha, herbimycin A, PNU 1451 56E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline. In yet another aspect, a cytokine may be selected from the group consisting of interleukin I (IL-I), IL-2, IL-5, IL-10, IL-11, IL-12, IL-18, interferonη-γ (IF-γ), IF-a, IF-, tumor necrosis factor-ct (TNF-ct), or GM-CSF (granulocyte macrophage colony stimulating factor). In still further embodiments of the invention, the agent may be a virus, a bacteriophage, a bacterium, a liposome, a microparticle, a magnetic bead, a yeast cell, a mammalian cell or a cell. In certain aspects, the virus is a lentivirus, a papovaviruses, a simian virus 40, a bovine papilloma virus, a polyoma virus, adenovirus, vaccinia virus, adeno-associated virus (AAV), or herpes virus. The agent may also be a eukaryotic expression vector, and more preferably a gene therapy vector.

The brain targeting peptides of the invention may be attached to a solid support, e g, an array or bead. Embodiments of the invention may also include an isolated peptidomimetic comprising a sequence that mimics a peptide motif selected from the group consisting Phe-Lys-Leu (FKL), Arg-Gly-Leu (RGL), Ser-Arg-Gly (SRG), Tyr-Val-Leu (YVL), Trp-Gly-Phe (WGF), Val-Leu-His (VLH), Leu-Tyr-Val (LYV), Leu-Trp-Gly (LWG), Leu-His-Ser (LHS), His-Ser-Arg (HSR), Gly-Leu-Trp (GLW), Gly-Phe-Lys (GFK), Arg-Leu-Ser (RLS), Gly-Ser-Val (GSV), Ser-Val-Ser (SVS), Leu-Gly-Ser (LGS), Val-Arg-Phe (VRF), Ser-Asn-Thr (SNT), Arg-Phe-Arg (RFR), Asn-Thr-Arg (NTR), Leu-Ser-Asn (LSN), Gly-Phe-Val (GFV), Phe-Val-Arg (FVR), Phe-Arg-Leu (FRL), Trp-Arg-Val (WRV), Phe-Ser-Leu (FSL), Val-Phe-Ser (VFS), Val-Ala-Trp (VAW), Ser-Leu-Phe (SLF), Arg-Val-Phe (RVF), Leu-Phe-Trp (LFW), Lys-Val-Ala (KVA), Phe-Trp-Lys (FWK), Ala-Trp-Arg (AWR), Val-His-Gly (VHG), Ser-Val-His (SVH), His-Gly-Val (HGV), Arg-Val-Cys (RVC), Arg-Pro-Gln (RPQ), Gln-Lys-Ile (QKI), Pro-Gln-Lys (PQK), Asn-Gly-Ala (NGA), Lys-Fle-Asn (KIN), Ile-Asn-Gly (ING), Gly-Arg-Pro (GRP), Gly-Ala-Arg (GAR), Ala-Arg-Val (ARV), Leu-Ser-Gly (LSG), Val-Asp-Ser (VDS), Ser-Val-Asp (SVD), or a peptidomimetic comprising a sequence that mimics a peptide consisting of SEQ. ID. NO. 1 to SEQ. ID. NO. 36, wherein the peptide is enriched in CSF and the brain.

Further embodiments include methods of targeting the delivery of an agent to CSF and brain, or vasculature thereof, in a subject, by obtaining an inventive brain targeting peptide as described herein or according to the inventive methods described herein, operatively coupling the peptide to the agent, and administering the peptide-coupled agent to the subject. A subject may be, but is not limited to, a primate, a monkey, a human, a mouse, a dog, a cat, a rat, a sheep, a horse, a cow, a goat or a pig. The agent can be a drug, a chemotherapeutic agent, a radioisotope, a pro-apoptosis agent, an anti-angiogenic agent, an enzyme, a hormone, a cytokine, a growth factor, a cytotoxic agent, a peptide, a protein, an antibiotic, an antibody, a Fab fragment of an antibody, an imaging agent, an antigen, a survival factor, an anti-apoptotic agent, a hormone antagonist, a virus, a bacteriophage, a bacterium, a hormone, a micro-particle, a magnetic bead, a micro-device, a yeast cell, a mammalian cell, a cell or an expression vector.

BRIEF DESCRIPTION OF THE FIGURES

FIG. 2A shows the enrichment of certain peptide motifs in the CSF of animal #1.1. FIG. 2B shows the enrichment of certain peptide motifs in the CSF of animal #1.2. FIG. 2C shows the enrichment of certain peptide motifs in the blood of animal #1.1. FIG. 2D shows the enrichment of certain peptide motifs in the blood of animal #1.2. The selection is much stronger in the CSF compartment as compared to the blood compartment.

FIG. 7A shows the percentage blood (black triangles) and CSF (grey triangles) Aβ40 reduction in rats injected with streptavidin pre-attached to brain shuttle peptide with SEQ. ID. NO. 8 and the BACE1 inhibitor peptide in a 3:1 ratio. FIG. 7B shows the percentage blood (black circles) and CSF (grey circles) Aβ40 reduction in rats injected with streptavidin pre-attached to only BACE1 inhibitor peptides (tetrameric display).

DETAILED DESCRIPTION OF EMBODIMENTS OF THE INVENTION

Definitions

Figure 1A:
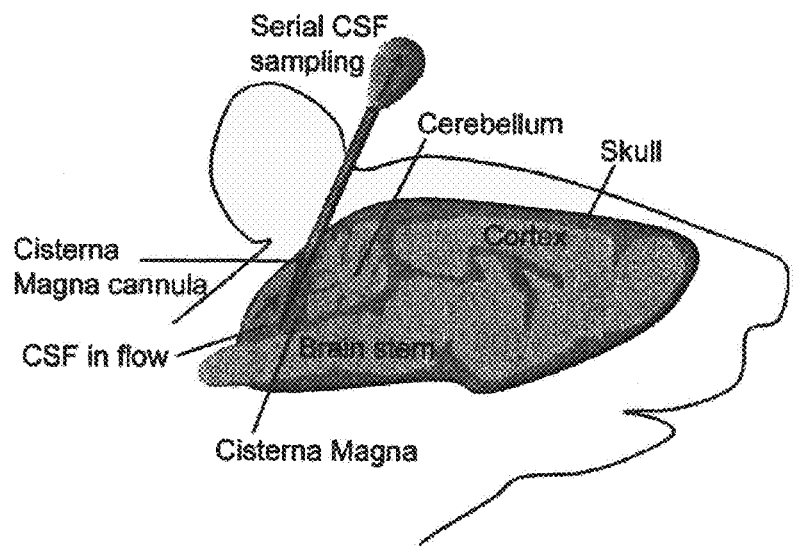
FIG. 1A is a schematic depiction of in vivo phage display screening and CSF sampling. In every selection round, phages are intravenously administered (tail vein) and subsequently recovered from CSF and blood, amplified, pooled, and used for the next selection round. Increased recovery of certain phage peptide clones in every subsequent round reflects the selection of peptides preferentially targeting the CSF.
Figure 1B:
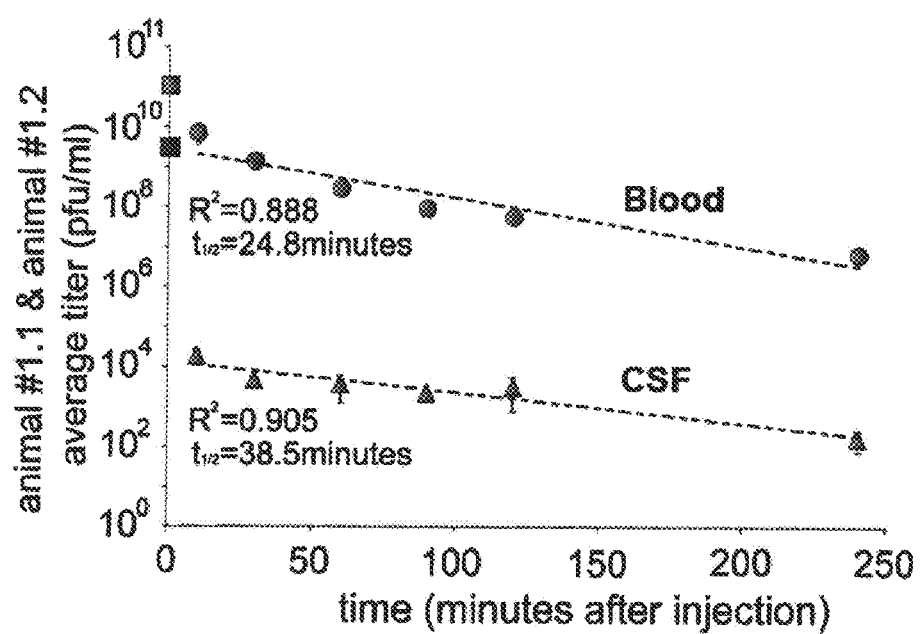
FIG. 1B illustrates the kinetic of phages in blood and CSF based on plaque forming units (pfu) for the first round of selection.
Figure 2A:
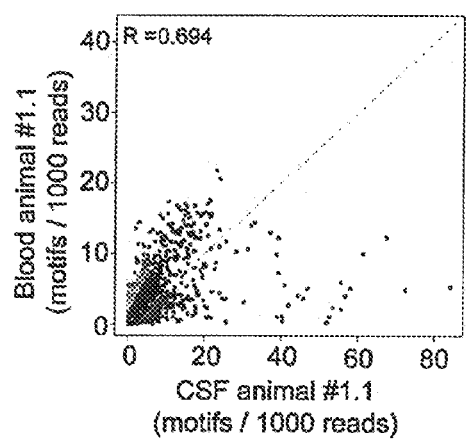
FIGS. 2A-2D show selection in CSF and blood after intravenously administered phage library. For each selection round, all tripeptide motifs extracted from the CSF isolated phage were pooled and sequenced. These figures show the enrichment of certain peptide motifs in CSF and blood.
Figure 2B:
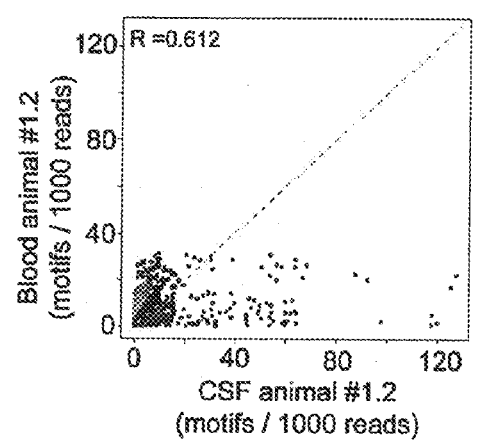
Figure 2C:
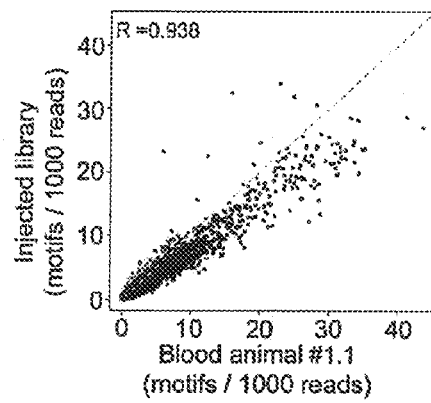
Figure 2D:
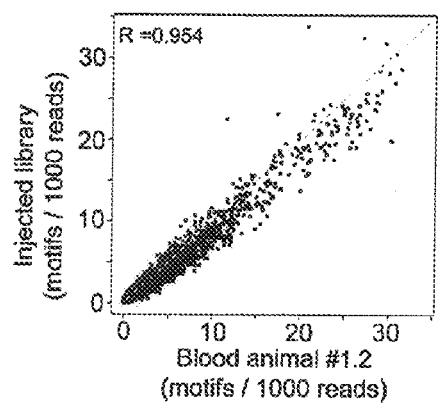
Figure 3:
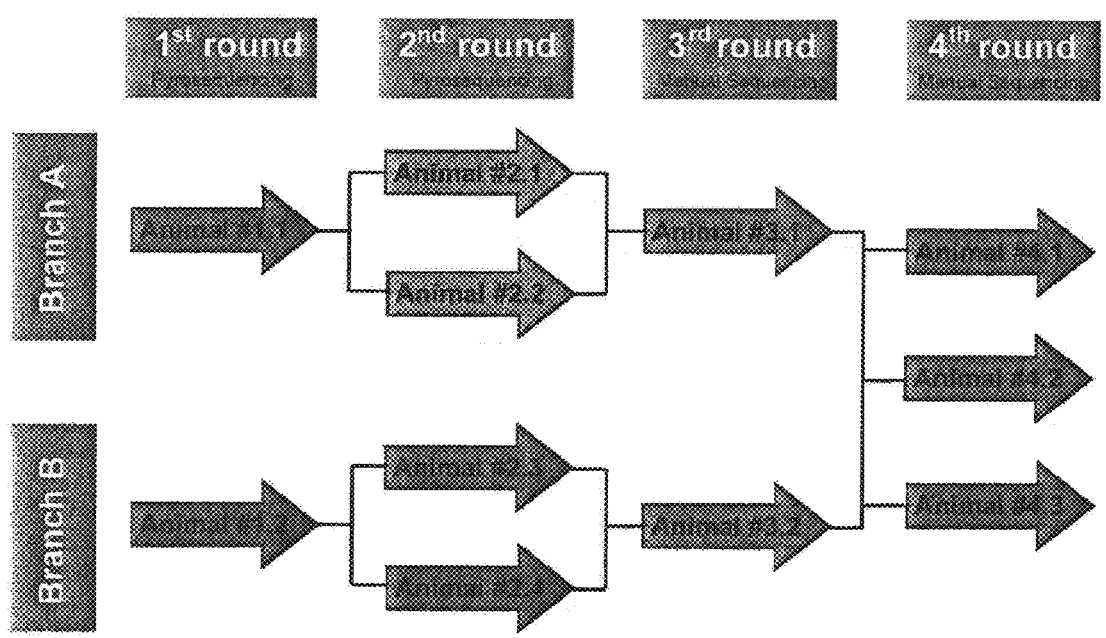
FIG. 3 shows the overall in vivo selection strategy over four rounds in rats, starting in two branches that merge in the final, fourth round of selection in three different animals.
Figure 4:
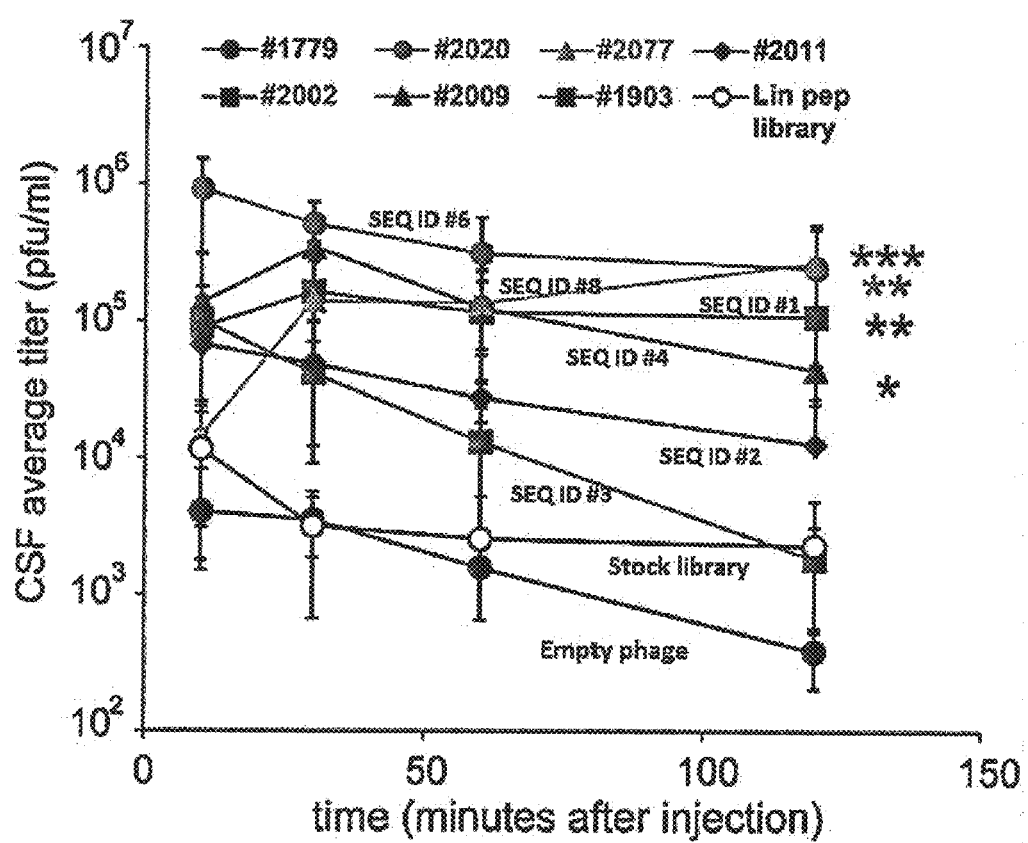
FIG. 4 shows specific phage clones in CSF and blood after four rounds of in vivo selection. The figure shows the data for some of the enriched peptides on phage particles compared to the empty phage. Many more phage clones (based on plaque forming units (pfu) were found in CSF compared to the empty phage.
Figure 5:
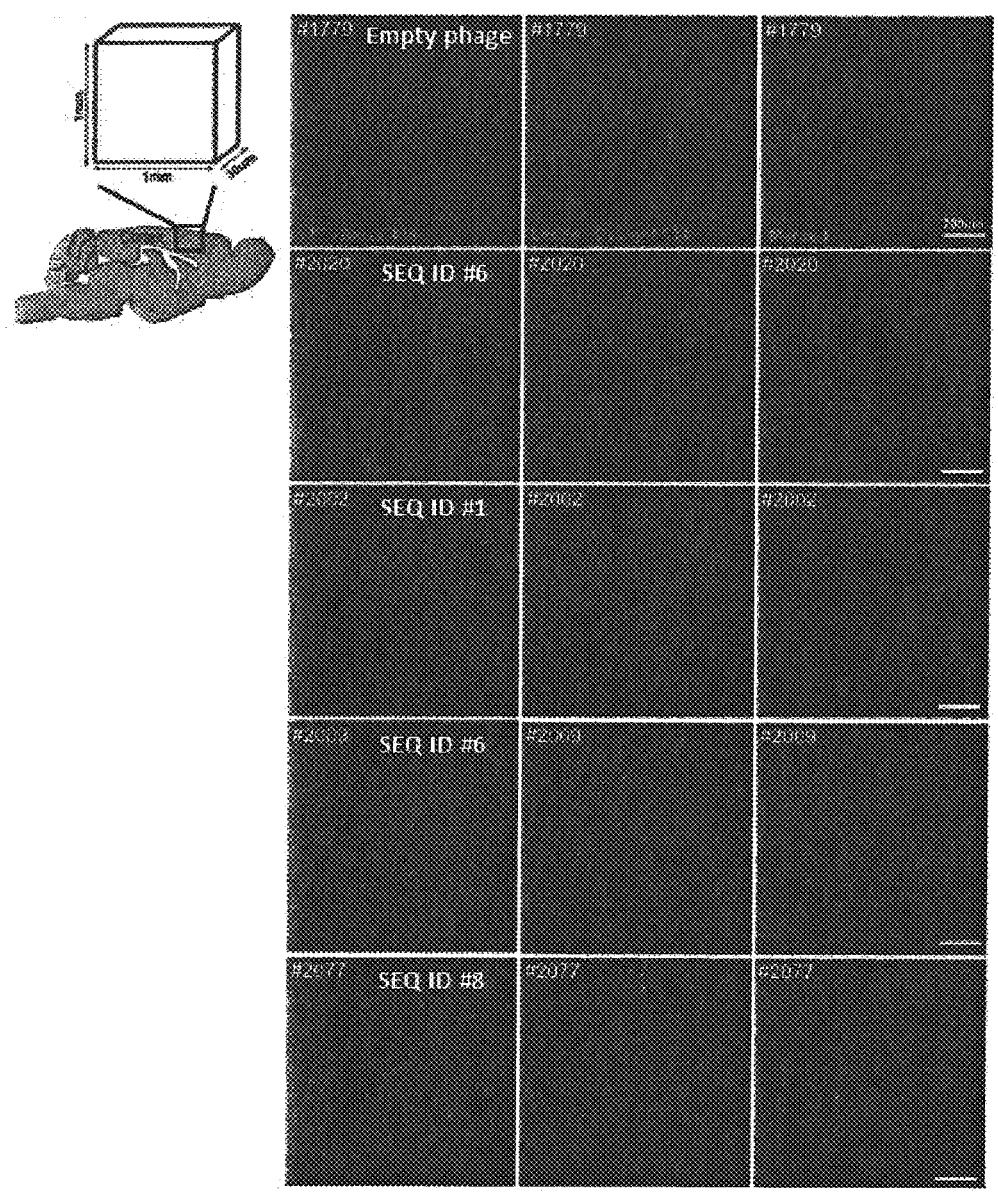
FIG. 5 shows specific phage clones bind to the vasculature in the brain. Specific phage clones were intravenously administered to allow targeting in vivo. Subsequently, immunohistochemistry was used to detect the phages specifically bound to the brain blood vessels and capillaries. No staining was observed with the empty phage while especially clone SEQ. ID. NO. 1, SEQ. ID. NO. 6 and SEQ. ID. NO. 8 showed strong and specific staining at brain capillaries in the cortex.
Figure 6A:
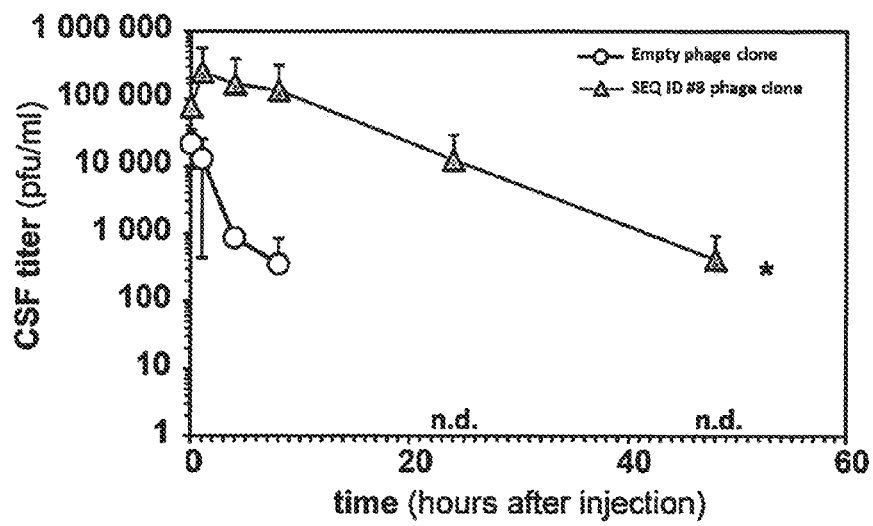
FIG. 6A shows that one specific peptide (SEQ. ID. NO. 8), synthesized and displayed on the T7 phage is found at higher concentrations in CSF than a control scrambled peptide.
Figure 6B:
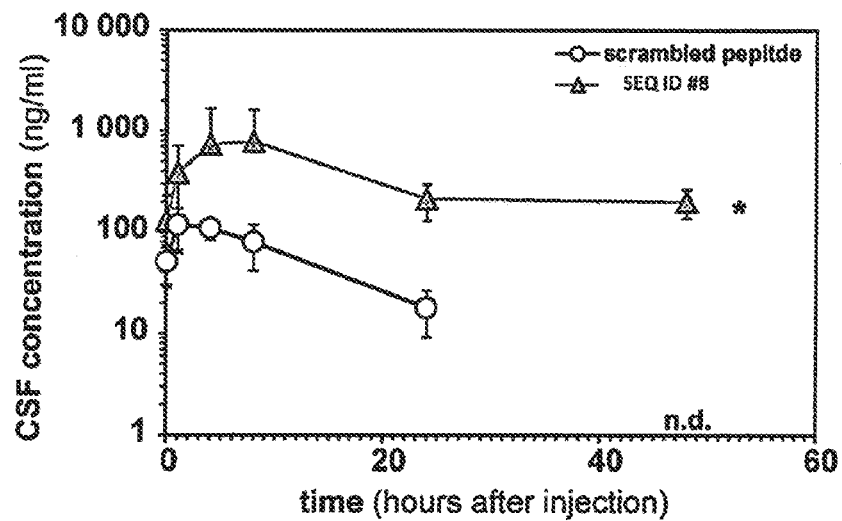
FIG. 6B shows that this is also the case when the peptide SEQ. ID. NO. 8 is linked to SA through an N-terminal biotin.
Figure 6C:
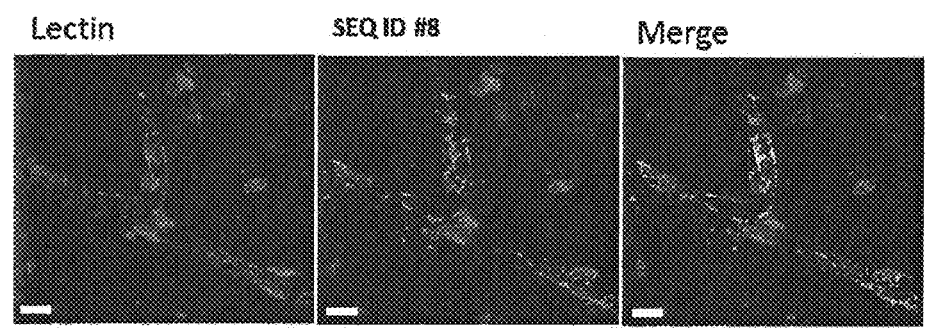
FIG. 6C shows the staining of SEQ. ID. NO. 8 phage clone colonializing with a brain vessel marker lectin at capillaries in the brain.

The "blood-brain barrier" or "BBB" refers to the physiological barrier between the peripheral circulation and the brain and spinal cord which is formed by tight junctions within the brain capillary endothelial plasma membranes, creating a tight barrier that restricts the transport of molecules into the brain, even very small molecules such as urea (60 Daltons). The BBB within the brain, the blood-spinal cord barrier within the spinal cord, and the blood-retinal barrier within the retina are contiguous capillary barriers within the CNS, and are herein collectively referred to the blood-brain barrier or BBB. The BBB also encompasses the blood-CSF barrier (choroid plexus) where the barrier is comprised of ependymal cells rather than capillary endothelial cells.

The "brain effector entity" refers to a molecule that is to be transported to the brain across the BBB. The effector entity typically has a characteristic therapeutic activity that is desired to be delivered to the brain. Effector entities include neurologically disorder drugs and neuroactive and cytotoxic agents such as e.g. peptides, proteins, enzymes and antibodies, in particular monoclonal antibodies or fragments thereof directed to a brain target.

A "brain targeting peptide" as used herein comprises at least a three amino acid peptide motif selected from the group consisting of Phe-Lys-Leu (FKL), Arg-Gly-Leu (RGL), Ser-Arg-Gly (SRG), Tyr-Val-Leu (YVL), Trp-Gly-Phe (WGF), Val-Leu-His (VLH), Leu-Tyr-Val (LYV), Leu-Trp-Gly (LWG), Leu-His-Ser (LHS), His-Ser-Arg (HSR), Gly-Leu-Trp (GLW), Gly-Phe-Lys (GFK), Arg-Leu-Ser (RLS), Gly-Ser-Val (GSV), Ser-Val-Ser (SVS), Leu-Gly-Ser (LGS), Val-Arg-Phe (VRF), Ser-Asn-Thr (SNT), Arg-Phe-Arg (RFR), Asn-Thr-Arg (NTR), Leu-Ser-Asn (LSN), Gly-Phe-Val (GFV), Phe-Val-Arg (FVR), Phe-Arg-Leu (FRL), Trp-Arg-Val (WRV), Phe-Ser-Leu (FSL), Val-Phe-Ser (VFS), Val-Ala-Trp (VAW), Ser-Leu-Phe (SLF), Arg-Val-Phe (RVF), Leu-Phe-Trp (LFW), Lys-Val-Ala (KVA), Phe-Trp-Lys (FWK), Ala-Trp-Arg (AWR), Val-His-Gly (VHG), Ser-Val-His (SVH), His-Gly-Val (HGV), Arg-Val-Cys (RVC), Arg-Pro-Gln (RPQ), Gln-Lys-Ile (QKI), Pro-Gln-Lys (PQK), Asn-Gly-Ala (NGA), Lys-Ile-Asn (KIN), Ile-Asn-Gly (ING), Gly-Arg-Pro (GRP), Gly-Ala-Arg (GAR), Ala-Arg-Val (ARV), Leu-Ser-Gly (LSG), Val-Asp-Ser (VDS), and Ser-Val-Asp (SVD). It has to be understood that the three amino acid peptide motifs in a brain targeting peptide of the present invention can be sequential and/or overlapping. For example, in case of overlapping motifs, the second amino acid of a first three amino acid motif can be the first amino acid of a second three amino acid motif and/or the third amino acid of the first amino acid motif can be the first amino acid of a third amino acid motif in the brain targeting peptide.

A "neurological disorder" as used herein refers to a disease or disorder which affects the CNS and/or which has an etiology in the CNS. Exemplary CNS diseases or disorders include, but are not limited to, neuropathy, amyloidosis, cancer, an ocular disease or disorder, viral or microbial infection, autoimmunity, inflammation, ischemia, neurodegenerative disease, seizure, behavioral disorders, and a lysosomal storage disease. For the purposes of this application, the CNS will be understood to include the eye, which is normally sequestered from the rest of the body by the blood-retina barrier. Specific examples of neurological disorders include, but are not limited to, neurodegenerative diseases (including, but not limited to, Lewy body disease, postpo-liomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia), cancer (e.g. of the CNS and/or brain, including brain metastases resulting from cancer elsewhere in the body), multiple sclerosis (relapsing remitting, primary progressive and secondary progressive forms).

A "neurological disorder drug" is a drug or therapeutic agent that treats one or more neurological disorder(s). Neurological disorder drugs of the invention include, but are not limited to, small molecule compounds, antibodies, peptides, proteins, natural ligands of one or more CNS target(s), modified versions of natural ligands of one or more CNS target(s), aptamers, inhibitory nucleic acids (i.e., small inhibitory RNAs (siRNA) and short hairpin RNAs (shRNA)), ribozymes, and small molecules, or active fragments of any of the foregoing. Exemplary neurological disorder drugs of the invention are described herein and include, but are not limited to: antibodies, aptamers, proteins, peptides, inhibitory nucleic acids and small molecules and active fragments of any of the foregoing that either are themselves or specifically recognize and/or act upon (i.e., inhibit, activate, or detect) a CNS antigen or target molecule such as, but not limited to, amyloid precursor protein or portions thereof, amyloid beta, beta-secretase, gamma-secretase, tau, alpha-synuclein, parkin, huntingtin, DR6, presenilin, ApoE, glioma or other CNS cancer markers, and neurotrophins. Non-limiting examples of neurological disorder drugs and the corresponding disorders they may be used to treat: Brain-derived neurotrophic factor (BDNF), Chronic brain injury (Neurogenesis), Fibroblast growth factor 2 (FGF-2), Anti-Epidermal Growth Factor Receptor Brain cancer, (EGFR)-antibody, Glial cell-line derived neural factor Parkinson's disease, (GDNF), Brain-derived neurotrophic factor (BDNF) Amyotrophic lateral sclerosis, depression, Lysosomal enzyme Lysosomal storage disorders of the brain, Ciliary neurotrophic factor (CNTF) Amyotrophic lateral sclerosis, Neuregulin-1 Schizophrenia, Anti-HER2 antibody (e.g. trastuzumab) Brain metastasis from HER2-positive cancer.

An "imaging agent" is a compound that has one or more properties that permit its presence and/or location to be detected directly or indirectly. Examples of such imaging agents include proteins and small molecule compounds incorporating a labeled entity that permits detection.

A "CNS antigen" or "brain target" is an antigen and/or molecule expressed in the CNS, including the brain, which can be targeted with an antibody or small molecule. Examples of such antigen and/or molecule include, without limitation: beta-secretase 1 (BACE1), amyloid beta (Abeta), epidermal growth factor receptor (EGFR), human epidermal growth factor receptor 2 (HER2), Tau, apolipoprotein E4 (ApoE4), alpha-synuclein, CD20, TREM2 huntingtin, prion protein (PrP), leucine rich repeat kinase 2 (LRRK2), parkin, presenilin 1, presenilin 2, gamma secretase, death receptor 6 (DR6), amyloid precursor protein (APP), p75 neurotrophin receptor (p75NTR), and caspase 6. In one embodiment, the antigen is BACE1.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

"Antibody fragments" herein comprise a portion of an intact antibody which retains the ability to bind antigen. Examples of antibody fragments include Fab, Fab', F(ab')2, and Fv fragments; diabodies; linear antibodies; single-chain antibody molecules such as, e.g. single chain Fab, scFv and multispecific antibodies formed from antibody fragments. The "Single chain Fab" format is e.g. described in Hust, M. et al. BMC Biotechnol. 2007 Mar. 8; 7:14.

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature, 256:495 (1975), or may be made by recombinant DNA methods (see, e.g., U.S. Pat. No. 4,816,567). The "monoclonal antibodies" may also be isolated from phage antibody libraries using the techniques described in Clackson et al., Nature, 352:624-628 (1991) and Marks et al., J. Mol. Biol., 222:581-597 (1991). Specific examples of monoclonal antibodies herein include chimeric antibodies, humanized antibodies, and human antibodies, including antigen-binding fragments thereof. The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al, Proc. Natl. Acad. Sci. USA, 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

The term "cytotoxic agent" as used herein refers to a substance that inhibits or prevents a cellular function and/or causes cell death or destruction. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof.

An "effective amount" of an agent, e.g., a pharmaceutical formulation, refers to an amount effective, at dosages and for periods of time necessary, to achieve the desired therapeutic or prophylactic result.

A "linker" as used herein refers to a chemical linker or a peptide linker that covalently connects the different entities of the blood brain barrier shuttle of the present invention. The linker connects for example the brain effector entity to brain targeting peptide of the present invention.

Peptide linkers, comprised of from one to twenty amino acids joined by peptide bonds, can be used. In certain embodiments, the amino acids are selected from the twenty naturally-occurring amino acids. In certain other embodiments, one or more of the amino acids are selected from glycine, alanine, proline, asparagine, glutamine and lysine. In other embodiments, the linker is a chemical linker. In certain embodiments, said linker is a single chain peptide with an amino acid sequence with a length of at least 25 amino acids, preferably with a length of 32 to 50 amino acids. In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is (G4S)4 (SEQ. ID. NO. 17). In one embodiment said linker is $(G_4S)_6G_2$ (SEQ. ID. NO. 13).

Conjugation may be performed using a variety of chemical linkers. For example, the brain shuttle peptide and the brain effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52: 127-131 (1992); U.S. Pat. No. 5,208,020) may be used.

Covalent conjugation can either be direct or via a linker. In certain embodiments, direct conjugation is by construction of a protein fusion (i.e., by genetic fusion of the two genes encoding the brain targeting peptide and effector entity and expressed as a single protein). In certain embodiments, direct conjugation is by formation of a covalent bond between a reactive group on one of the two portions of the brain shuttle peptide and a corresponding group or acceptor on the brain effector entity. In certain embodiments, direct conjugation is by modification (i.e., genetic modification) of one of the two molecules to be conjugated to include a reactive group (as non-limiting examples, a sulfhydryl group or a carboxyl group) that forms a covalent attachment to the other molecule to be conjugated under appropriate conditions. As one non-limiting example, a molecule (i.e., an amino acid) with a desired reactive group (i.e., a cysteine residue) may be introduced into, e.g., the brain shuttle peptide and a disulfide bond formed with the neurological drug. Methods for covalent conjugation of nucleic acids to proteins are also known in the art (i.e., photocrosslinking, see, e.g., Zatsepin et al. Russ. Chem. Rev. 74:77-95 (2005)) Conjugation may also be performed using a variety of linkers. For example, a brain shuttle peptide and a effector entity may be conjugated using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Peptide linkers, comprised of from one to twenty amino acids joined by peptide bonds, may also be used. In certain such embodiments, the amino acids are selected from the twenty naturally-occurring amino acids. In certain other such embodiments, one or more of the amino acids are selected from glycine, alanine, proline, asparagine, glutamine and lysine. The linker may be a "cleavable linker" facilitating release of the effector entity upon delivery to the brain. For example, an acid-labile linker, peptidase-sensitive linker, photolabile linker, dimethyl linker or disulfide-containing linker (Chari et al, Cancer Res. 52: 127-131 (1992); U.S. Pat. No. 5,208,020) may be used.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "phage display library" refers to a plurality of phage in which a random heterologous peptide has been engineered into a phage capsid protein and presented on the phage surface. In certain aspects, the peptide may be constrained by cysteine residues of the peptide. The methods may further comprise administering phage isolated from the second subject to at least a third subject, obtaining samples of one or more tissues or fluid including CSF from the third subject, and identifying the peptide sequence displayed by phage isolated from the tissues or fluid including CSF of the third subject. In certain aspects, the administration of phage is by injection, preferably intravenous injection. The subject may be a mammal, and in particular aspects the mammal is a rodents, non-human primates or humans. The methods may further compose amplifying the phage isolated from the samples of one subject prior to administration to an additional subject. Amplifying may entail PCR amplification of all or part of a phage nucleic acid followed by cloning the amplified fragment into a second phage, and/or multiplication of phage through a phage host organism, for example bacteria that support phage replication.

The term "in vivo cerebrospinal fluid (CSF) sampling" refers to specifically obtain CSF samples in a subject. The subject may be a mammal, and in particular aspects the mammal is a rodents, non-human primates or humans. The sample is obtained using a cannula inserted in the cisterna magna as specifically describe in this application.

The term "simultaneously" may be used to mean that samples are obtained in a time interval (minutes to hours to days) that accommodates the taking of samples from CSF. Other embodiments of the invention include isolated peptides identified by the methods described herein.

The term "peptide motif refers to a three amino acids peptide sequence with the ability to target or bind a certain tissue or receptor or with the ability to be transported over the BBB or BCSFB.

As used herein "selective binding" in no way precludes binding to other cells or material, but means the preferential binding of a target tissue, organ, vasculature or receptor thereof. Selective binding may include a 2, 3, 4, 5, 6, 7, 8, 9, 10 or more-fold preference for a selected tissue/target as compared to a non-selected tissue/target.

A "brain targeting peptide" as used herein is a peptide comprising at least one peptide motif as defined herein which is characterized by selective localization to CSF and/or brain or vasculature thereof. The brain targeting peptide can comprise more than one peptide motif and the peptide motifs can be contiguous or be separated by non-motif amino acid sequences.

Selective localization may be determined, for example, by methods disclosed below, wherein the putative targeting peptide sequence is incorporated into a protein that is displayed on the outer surface of a phage. Administration to a subject of a library of such phage that have been genetically engineered to express a multitude of such targeting peptides of different amino acid sequences is followed by collection of CSF or brain derived from one or more subjects and identification of phage found in or associated with that fluid or organ. A phage expressing a targeting peptide sequence is considered to be selectively localized to a fluid or organ if it exhibits greater binding or localization in that fluid or organ as compared to a control fluid or organ. Preferably, selective localization of a targeting peptide should result in a two-fold or higher enrichment of the phage or peptide in the target fluid or organ, compared to a control fluid or organ. Selective localization resulting in at least a three-fold, four-fold, five-fold, six-fold, seven-fold, eight-fold, nine-fold, ten-fold or higher enrichment in the target fluid or organ, as compared to a control organ, is more preferred. Alternatively, a phage expressing a targeting peptide sequence that exhibits selective localization preferably shows an increased enrichment in the target fluid or organ as compared to a control fluid or organ when phage recovered from the target or selected fluid or organ are injected into or put in contact with a second, third, fourth or more subjects for additional screening. Another alternative means to determine selective localization or binding of the phage expressing the putative target peptide preferably exhibit a two-fold, more preferably a three-fold or higher enrichment in the target fluid or organ as compared to control phage that express a non-specific peptide or that have not been genetically engineered to express any putative target peptides. Yet another means to determine selective localization is that localization to the target fluid or organ of phage expressing the target peptide is at least partially blocked by the coadministration of a synthetic peptide containing the target peptide sequence.

Cerebrospinal Fluid In Vivo Selection

Vascular mapping by in vivo phage display reveals selectively expressed biochemical "addresses" within different vasculatures. This type of approach has been used to discover ligand-receptor systems that can be used for the delivery of agents to specific tissues (Arap et al, 1998, Pasqualini et al, 1996, Arap et al, 2002, Kolonin et al, 2001, Pasqualini et al, 2000). This screening approach is based on the ability of short ligand peptides from combinatorial libraries (displayed on an M13-based phage vector) to target a specific organ after systemic administration (Pasqualini et al, 2000). Peptides targeting tissues and disease states have been isolated and, in some cases, led to the identification of the corresponding vascular receptors (Arap et al, 1998, Pasqualini et al, 1996, Arap et al, 2002, Kolonin et al, 2001, Rajotte and Ruoslahti, 1999, Kolonin, et al, 2002, Kolonin et al, 2004). Notably, investigators have reported the use of a phage display library in a cancer patient. One of the ligand motifs identified as an interleukin-11-like peptide and its targeting to the interleukin-11 receptor is being exploited as a potential strategy for targeted therapeutic delivery in human prostate cancer (Zurita et al, 2004). A key step of the selection of phage display random peptide libraries in vivo is the sampling strategy, thus how and where the phages are recovered. Preferably, the in vivo selection strategy should be based on not only binding to a tissue or a receptor but also included a functional step as transport over a cellular barrier for example. This is particular important when the aim is to identify novel transport systems involving the blood brain barrier (BBB) or the blood CSF barrier (BCSFB).

In certain instances, one may desire to obtain highly enriched samples which is not only dependent on binding but also on transport over a cellular membrane. In these situations, typical screening procedures are not optimal, thus the procedures described herein provide a more efficient method of identifying targeting peptides with characteristics amenable to development into drugs, targeting, or diagnostic agents. The methodology described herein is used to further enrich the selected phage population and to select various peptides based on both binding and transport properties. A single screen in a single live subject selects a subpopulation of peptides, but this population needs to be enriched for selective and transport peptides. The inventor provides an improved methodology to acquire an enrichment of targeting peptides that may be utilized in, for example, human subjects. A "subject" refers generally to a mammal. In certain preferred embodiments, the subject is a rodent, a primate, a monkey, or a human. In more preferred embodiments, the subject is a human.

Identification of Targeting Peptides

The invention comprises methods for the identification of one or more brain targeting peptides or molecular targets that could be utilized for the localization of a composition to CSF, brain or associated vasculature. Screening of the fluid and organs of a subject for peptides with N residues, wherein N can be 5, 6, 7, 8, 9, 10, 11, 12, 13, 14, 15 or more residues, random phage library that yield several peptide motifs. In one example, various clones comprising tri-peptide motifs Phe-Lys-Leu (FKL), Arg-Gly-Leu (RGL), Ser-Arg-Gly (SRG), Tyr-Val-Leu (YVL), Trp-Gly-Phe (WGF), Val-Leu-His (VLH), Leu-Tyr-Val (LYV), Leu-Trp-Gly (LWG), Leu-His-Ser (LHS), His-Ser-Arg (HSR), Gly-Leu-Trp (GLW), Gly-Phe-Lys (GFK), Arg-Leu-Ser (RLS), Gly-Ser-Val (GSV), Ser-Val-Ser (SVS), Leu-Gly-Ser (LGS), Val-Arg-Phe (VRF), Ser-Asn-Thr (SNT), Arg-Phe-Arg (RFR), Asn-Thr-Arg (NTR), Leu-Ser-Asn (LSN), Gly-Phe-Val (GFV), Phe-Val-Arg (FVR), Phe-Arg-Leu (FRL), Trp-Arg-Val (WRV), Phe-Ser-Leu (FSL), Val-Phe-Ser (VFS), Val-Ala-Trp (VAW), Ser-Leu-Phe (SLF), Arg-Val-Phe (RVF), Leu-Phe-Trp (LFW), Lys-Val-Ala (KVA), Phe-Trp-Lys (FWK), Ala-Trp-Arg (AWR), Val-His-Gly (VHG), Ser-Val-His (SVH), His-Gly-Val (HGV), Arg-Val-Cys (RVC), Arg-Pro-Gln (RPQ), Gln-Lys-Ile (QKI), Pro-Gln-Lys (PQK), Asn-Gly-Ala (NGA), Lys-Ile-Asn (KIN), Ile-Asn-Gly (ING), Gly-Arg-Pro (GRP), Gly-Ala-Arg (GAR), Ala-Arg-Val (ARV), Leu-Ser-Gly (LSG), Val-Asp-Ser (VDS), Ser-Val-Asp (SVD) exhibited high frequency, selective targeting or binding and presence in CSF and brain. Comparison of the selected peptide motifs with available sequences in on-line protein databases suggests that a number of candidate proteins share homologous or similar sequences with these peptides motifs. Mechanistic studies surrounding these motifs are being pursued to provide a novel platform for the identification of peptides and targets for the targeting of CSF fluid and brain, and associated vasculature as well as combinations of such. The findings will also have important clinical implications in that newly identified motifs may serve as peptidomimetic drug leads and can be optimized to direct delivery of various therapeutic moieties. One method includes injecting the phage libraries intravenously and recovers samples after a few minutes.

A "phage display library" is a collection of phage that has been genetically engineered to express a set of putative targeting peptides on their outer surface. In preferred embodiments, DNA sequences encoding the putative targeting peptides are inserted in frame into a gene encoding a phage capsid protein. In other preferred embodiments, the putative targeting peptide sequences are in part random mixtures of all twenty amino acids and in part non-random. In certain preferred embodiments the putative targeting peptides of the phage display library exhibit one or more cysteine residues at fixed or random locations within the targeting peptide sequence. Cysteines may be used, for example, to create a cyclic peptide. Targeting peptides selectively binding different organ, tissue or cell type can be isolated by "biopanning" (Pasqualini and Ruoslahti, 1996, Pasqualini, 1999) In brief, a library of phage containing putative targeting peptides is administered to an animal, and samples of organs, tissues, fluid or cell types containing phage are collected. In preferred embodiments utilizing lytic phage, the phage may be propagated in vitro between rounds of biopanning in bacteria. The bacteria are lysed by the phage to secrete multiple copies of the phage that display a particular insert. Phages that bind to a target molecule or were transported into a specific fluid or tissue can be collected from the target fluid and organ, and then amplified by growing them in host bacteria. If desired, the amplified phage can be administered to a host and samples of fluid and organs, and then again collected. Multiple rounds of biopanning can be performed until a population of selective binders and transporters is obtained. The amino acid sequence of the peptides is determined by sequencing the DNA corresponding to the targeting peptide insert in the phage genome. The identified targeting peptide can then be produced as a synthetic peptide by standard protein chemistry techniques. This approach allows circulating targeting peptides to be detected in an unbiased functional assay, without any preconceived notions about the nature of their target. Once a candidate target is identified as the receptor of a targeting peptide, it can be isolated, purified and cloned by using standard biochemical methods. In certain embodiments, a subtraction protocol may be used to further reduce background phage binding. The purpose of subtraction is to remove phage from the library that bind to tissues other than the tissue of interest. In alternative embodiments, the phage library may be prescreened against a subject who does not possess the selected fluid, tissues or organs. The phage display technique involves genetically manipulating bacteriophage so that small peptides can be expressed on their surface (Smith and Scott, 1985 and 1993). The potential range of applications for this technique is quite broad, and the past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that serve as leads to the development of peptidomimetic drugs or imaging agents (Arap et al, 1998a) in addition to peptides, larger protein domains such as single-chain antibodies can also be displayed on the surface of phage particles (Arap et al, 1998a).

Choice of Phage Display System

Previous in vivo selection studies performed in mice preferentially employed libraries of random peptides expressed as fusion proteins with the gene III capsule protein in the fUSE5 vector (Pasqualini and Ruoslahti, 1996). The preferred phage system used for identifying transporter peptide is the T7 phage system. The T7 phage particle is very small (about 50 nm in diameter) allow transporting through cells using natural organelle intracellular sorting. The M13 phage system is significantly larger in size and may prevent cellular uptake and intracellular sorting.

Hence, prevent enrichment of target peptide in fluids and organs protected by cellular membranes such the blood brain barrier (BBB) and the blood CSF barrier (BCSFB). The number and diversity of individual clones present in a given library is a significant factor for the success of in vivo selection. It is preferred to use primary libraries, which are less likely to have an overrepresentation of defective phage clones. It is preferred to use primary libraries with a high diversity with equal proportion of all phage clones. The preparation of a library should be optimized to between $10^8$-$10^9$ plaque forming units (pfu)/ml. In certain embodiments, a bulk amplification strategy is applied between each round of selection. Phage libraries displaying linear, cyclic, or double cyclic peptides may be used within the scope of the present invention. However, phage libraries displaying 5, 6, 7, 8, 9, 10, 11, 12, 13, 14, 15 or more residues are preferred. Cyclic libraries are also preferred. However, the production of the cognate synthetic peptides, although possible, can be complex due to the multiple conformers with different disulfide bridge arrangements.

Targeted Delivery

Peptides that targets to vasculature have been coupled to cytotoxic drugs or proapoptotic peptides to yield compounds that were more effective and less toxic than the parental compounds.

The present invention describes methods and compositions for the selective targeting of CSF fluid and brain. A "receptor" for a targeting peptide includes but is not limited to any molecule or macromolecular complex that binds directly or indirectly to a targeting peptide. Non-limiting examples of receptors include peptides, proteins, glycoproteins, lipoproteins, epitopes, lipids, carbohydrates, multimolecular structures, and a specific conformation of one or more molecules. In preferred embodiments, a "receptor" is a naturally occurring molecule or complex of molecules that is present on the surface of cells within a target tissue or organ. Preferably, a "receptor" is a naturally occurring molecule or complex of molecules that is present on or in a tissue, organ, blood stream or vasculature thereof. More preferably, a "receptor" is a transport receptor that is internalized on a cell and transported to the opposite side of the cell using a transcytosis mechanism. In certain embodiments, therapeutic agents may be attached to a targeting peptide or fusion protein for selective delivery to, for example, the CSF and the brain. Agents or factors suitable for use may include any chemical compound or biologies that have a treatment effect on a brain disease. Chemotherapeutic agents and methods of administration, dosages, etc. are well known to those of skill in the art (see for example, the "Physicians' Desk Reference", Goodman & Oilman's "The Pharmacological Basis of Therapeutics" and in "Remington's Pharmaceutical Sciences" 15th ed, pp 1035-1038 and 1570-1580, each incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject.

Pharmaceutical Compositions

Where clinical applications are contemplated, it may be necessary to prepare pharmaceutical compositions-expression vectors, virus stocks, proteins, antibodies and drugs in a form appropriate for the intended application. Generally, this will entail preparing compositions that are essentially free of impurities that could be harmful to humans or animals. One generally will desire to employ appropriate salts and buffers to render delivery vectors stable and allow for uptake by target cells. Buffers also are employed when recombinant cells are introduced into a patient. Aqueous compositions of the present invention may comprise an effective amount of a protein, peptide, antibody, fusion protein, recombinant phage and/or expression vector, dissolved or dispersed in a pharmaceutically acceptable carrier or aqueous medium. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions The active compositions of the present invention may include classic pharmaceutical preparations. Administration of these compositions according to the present invention is via any common route so long as the target fluid, tissue or organ is available via that route. This includes oral, nasal, buccal, rectal, vaginal or topical. Alternatively, administration may be by orthotopic, intradermal, subcutaneous, intramuscular, intrapentoneal, intraarterial or intravenous injection. Such compositions normally would be administered as pharmaceutically acceptable compositions, described supra. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The earner can be a solvent or dispersion medium containing, for example, water, ethanol, (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, paraberis, chiorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin. Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques which yield a powder of the active ingredient plus any additional desired ingredient from a previously sterile-filtered solution thereof.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Surgical Implantation of the Cannula in the Cisterna Magna

The cisterna magna (CM) was cannulated using modification of methods previously described by Sarna et al. (1983) (Waring et al. 2010, 192 249-253) (Sarna et al. 1983, 383-388). Anesthetized Wistar rats (200-350 g) were mounted onto a stereotaxic device and a median incision was made on the top of the shaved head all the way back to the inter-scapular region. Two holes were drilled at the parietal region and mounting screws were secured in the holes. An additional hole was drilled at the external occipital crest and used to stereotactical guide the cannula into the CM. Dental cement was applied around the cannula and the screws to hold it in place. After the cement dried, the skin wound was sutured with a 4/0 supramid yarn. A spontaneous flow of cerebrospinal fluid (CSF) occurs when the cannula is placed well. The rats were removed from the stereotaxic apparatus, received appropriate post-operative analgesic treatment and allowed to recover for at least one week until no sign of blood in the CSF was observed. All animal procedures were fully approved by the institutional animal care authorities (Permission #2474).

Example 2: Serial Collection of CSF and Blood from Non-Anesthetized Adult Rats

The CM cannulated awake rats were gently held in the hand. The mandrain was pulled out of the cannula and 10 µL of the spontaneous flowing CSF was collected. Only clear CSF samples with no sign of blood contamination or discoloration were included in this study since patency of the cannula was eventually compromised. In parallel 10-20 µL blood from a small incision of the tip of the tail was collected in heparin (Sigma Aldrich) containing tubes. CSF and blood was collected at different time points after intravenous injection of the bacteriophages. Prior to collecting every CSF sample 10-15 μL of fluid was discarded, which represents the catheter dead volume.

Example 3: T7 Phage Peptide Library Engineering

Library was constructed using the T7Select 10-3b vector as outlined in the T7Select System Manual (Novagen) (Rosenberg et al. InNovations 6, 1-6 1996). Briefly, random 12-mer insert DNA was synthesized in the following format:

```
                                       (SEQ. ID. NO. 37)
5'-GGGGATCCGAATTCT(NHH)₁₂TAAGCTTGCGGCCGCA-3'

(SEQ. ID. NO. 38)
←3'-TCGAACGCCGGCGT-5'
```

NHH codons were used to avoid two stop codons and an overrepresentation of amino acids within the insert. N stands for a hand-mixed equimolar ratio of each nucleotide and H is a hand-mixed equimolar of both adenine and cytosine nucleotides. The single stranded regions were converted to duplex DNA by continuing incubation at 37° C. with dNTPs (Novagen) and Klenow enzyme (New England Biolabs) in Klenow Buffer (New England Biolabs) for 3 h. After the reaction, double-stranded DNA was recovered by EtOH precipitation. The obtained DNA was digested with EcoRI and Hindlll restriction enzymes (both from Roche). The digested and purified (QIAquick, Qiagen) inserts were then ligated (T4 ligase, New England Biolabs) into the predigested T7 vector in-frame after amino acid 348 of the capsid 10B gene. The ligation reaction was incubated at 16° C. for 18 h and subsequently subjected to in vitro packaging. The in vitro packaging into phages was performed according to the instructions attached to the T7Select 10-3b cloning Kit (Novagen) and the packaging solution was amplified once using E. coli (BLT5615, Novagen) until lysis. The lysate was centrifuged, tittered and frozen as glycerol stocks at −80° C.

Example 4: PCR Phage Identification

Variable regions of broth or plate amplified phage were directly subject of PCR amplification using in-house designed 454/Roche-amplicon fusion primers. The forward fusion primer contains sequences flanking the variable region (NNK)12 (template specific), the GS FLX Titanium Adapter A and a four base library key sequence (TCAG):

```
                                       (SEQ. ID. NO. 39)
5'-CCATCTCATCCCTGCGTGTCTCCGACTCAGGGAGCTGTCGTATTCCA
GTC-3'
```

The reverse fusion primer also carries a biotin for the attachment on a capture bead and the GS FLX Titanium Adapter B necessary for the clonal amplification during the emulsion PCR:

```
                                       (SEQ. ID. NO. 40)
5'-Biotin-CCTATCCCCTGTGTGCCTTGGCAGTCTCAGAACCCCTCA
AGACCCGTTTA-3'
```

The amplicon was then subjected to 454/Roche pyrosequencing according to the 454 GS-FLX Titanium protocol. For the manual Sanger sequencing (Applied Biosystems Hitachi 3730 xl DNA Analyzer) the T7 phage DNA was PCR amplified and sequenced with the following primer pairs:

```
PCR Forward:
                                       (SEQ. ID. NO. 41)
5'-AGTACGCAATGGGCCACG-3'

PCR Reverse:
                                       (SEQ. ID. NO. 42)
5'-GAGCGCATATAGTTCCTCC-3'

Sequencing Forward:
                                       (SEQ. ID. NO. 43)
5'-CAGGAGCTGTCGTATTCC-3'

Sequencing Reverse:
                                       (SEQ. ID. NO. 44)
5'-AAAAACCCCTCAAGACCCG-3'
```

The inserts of individual phage plaques were PCR amplified using the Roche Fast Start DNA Polymerase Kit (according to the manufacturer's instructions). A hot start (95° C. for 10 min) and 35 amplification cycles at 95° C. for 50 sec, 50° C. for 1 min and 72° C. for 1 min were performed.

Example 5: Phage Preparation, Application and Selection

Phages from the library, wt phages, the CSF and blood recovered phages or individual clones were amplified in Escherichia coli BL5615 in either broth medium (TB medium) (Sigma Aldrich) or on 500 cm² plates (Thermo Scientific) at 37° C. for 4 h. Phages were extracted from plates by either rinsing the plates with Tris-EDTA buffer solution (Fluka Analytical) or picking the plaques with a sterile pipette tip. Phages were recovered from either the culture supernatant or the extraction buffer by one round of polyethylene glycol precipitation (PEG 8000) (Promega) and resuspended in Tris-EDTA buffer solution.

The amplified phages underwent 2-3 rounds of endotoxin removal using endotoxin removal beads (Miltenyi Biotec) before intravenous (i.v.) injection. The phage contents in the CSF and blood samples harvested at the indicated time points were determined by a plaque counting assay according to the manufacturer's instructions (T7Select System Manual). Phage selection was carried out by i.v. tail vein injection of the purified library or by reinjection of the CSF recovered phages of the previous selection round. Subsequently, CSF and blood samples were collected at 10 min, 30 min, 60 min, 90 min, 120 min, 180 min, and 240 min after injection. A total of four rounds of in vivo panning were performed in which two selection branches were kept and analyzed separately during the first three selection rounds. All CSF recovered phage inserts of the first two selection rounds were subjected to 454/Roche pyro-sequencing whereas all CSF recovered clones of the last two selection rounds were manually sequenced. All blood harvested phages of the first selection round were also 454/Roche pyro-sequenced.

Example 6: Filter and Process Read Data

Roche-454 raw data is converted from binary standard flowgram format (sff, ncbi.nlm.nih.gov/Traces/trace.cgi?cmd=show&f=formats&m=doc&s=format#sff) to human readable Pearson format (fasta, emboss.sourceforge.net/docs/themes/SequenceFormats.html) by using vendor software (454.com/mv454/documentation/gs-flxsys-tem/emanuals/Part_C/wwhelp/wwhimpl/js/html/wwhelp.htm#href=PartC.1.087.html#9003035). Further nucleotide sequence processing is performed with in-house developed C-programs and scripts (unpublished software package) as described in the following.

The primary data analysis consists of stringent multi-step filtering procedures. In order to filter away reads that do not contain valid 12 mer insert DNA sequences, reads are successively aligned to the start tag defined as the nucleotide sequence GTGATGCTCGGGGATCCGAAT TCT (SEQ. ID. NO. 45), stop tag TAAGCTTGCGGCCGCACTCGAGTA (SEQ. ID. NO. 46), and background insert CCTGCAGGGATATCCCGGGAGCTCGTCGAC (SEQ. ID. NO. 47) by performing a global Needleman-Wunsch alignment allowing up to 2 mismatches per alignment (Needleman et al, 1970). Accordingly, reads without start or stop tag and reads containing the background insert, i.e. alignments that exceeded the allowed number of mismatches, are removed from the library. As for the remaining reads, the N-mer DNA sequence stretches beginning with the start tag and ending before the stop tag are cut out from the original read sequence and processed further (in the following named "inserts"). Upon translation of the insert, the part after the first stop codon from the 5-prime end is removed from the insert. In addition, nucleotides leading to incomplete codons at the 3-prime end were also removed. In order to exclude inserts containing only the background sequence, translated inserts beginning with the amino acid pattern "PAG" are removed as well. Peptides of length shorter than 3 amino acids upon translation are discarded from the library. Finally, redundancies in the insert library are removed, and the frequency of each unique insert is calculated. The result of this analysis consists of a list nucleotide sequences (inserts) and its (read) frequencies.

Example 7: Grouping N-Mer DNA Inserts by Sequence Similarity

In order to overcome Roche-454 specific sequencing errors (e.g. problem of sequencing homopolymer stretches) and remove less trivial redundancies (for example due to sequencing errors), previously filtered N-mer insert DNA sequences (inserts) are categorized into groups of similar inserts (where up to 2 mismatches are allowed) by an iterative algorithm defined as follows: Inserts are sorted primarily by their frequency (highest to smallest) and secondary, in case of equal frequencies, by their length (longest to shortest). Consequently, the most frequent and longest insert defines the first "group", and the "group frequency" was set equal to the frequency of the insert. Subsequently, every remaining insert in the sorted list is attempted to be added to the group by pair-wise Needleman-Wunsch alignment. If the number of mismatches, insertions, or deletions in the alignment does not exceed the threshold of 2, then the insert is added to the group and the frequency of the insert is accordingly added to the total group frequency. Inserts added to a group are flagged as used and excluded from further processing. If an insert sequence cannot be added to an already existing group, then the insert is used to create a new group with the corresponding insert frequency and its flagged is set to "used" accordingly. The iteration finishes when every insert sequence was either utilized to form a new group or could be included into an already existing group. After all, grouped inserts composed of nucleotides are translated into peptide sequences (peptide library). The result of this analysis is a list of "grouped inserts" and their corresponding frequencies which accounts for the number of sequenced reads per insert.

Example 8: Motif Generation and Normalization

On the basis of the list of unique peptides, a library containing all possible amino acid patterns is generated as follows. Every possible amino acid pattern of length 3 (e.g. "ABC") are extracted from the peptides and together with its reverse pattern (e.g. "CBA") added to a universal motif library containing all possible patterns. This highly redundant motif library is sorted and redundancies are removed. Then, each motif in the library is iteratively tested whether it is present in the peptide library. If this is the case, then the frequencies of the peptides where the motif is found are added and assigned to the motif in the motif library. These frequencies are called "motif counts". The result of the motif generation is a two-dimensional array containing all occurring 3-amino acid patterns (motifs) and their corresponding motif counts which are a measure for the number of sequencing reads that lead to the corresponding motif upon filtering, grouping and translation of the read as described in detail above.

Finally, motif counts were normalized per sample using the following formula $$v_i = 10^2 n_i / \Sigma_j n_j$$

where $n_i$ is the number of reads that contain the motif i. Thus, $v_i$ denotes the frequency in % of reads (or peptides) in a sample that contain motif i. P-values of unnormalized motif counts were calculated with Fisher's exact test.

Example 9: Tripeptide Motif Hits after 4 Round of In Vivo Selection in Rats Using CSF Sampling The invention composes methods for the identification of one or more targeting peptides or molecular targets that could be utilized for the localization of a composition to CSF, brain or associated vasculature. Screening of the fluid and organs of a subject with X(N), wherein N can be 7, 8, 9, 10, 11, 12 or more residues, random phage library that yield several peptide motifs. In one example, various clones (comprising tripeptide motifs Phe-Lys-Leu (FKL), Arg-Gly-Leu (RGL), Ser-Arg-Gly (SRG), Tyr-Val-Leu (YVL), Trp-Gly-Phe (WGF), Val-Leu-His (VLH), Leu-Tyr-Val (LYV), Leu-Trp-Gly (LWG), Leu-His-Ser (LHS), His-Ser-Arg (HSR), Gly-Leu-Trp (GLW), Gly-Phe-Lys (GFK), Arg-Leu-Ser (RLS), Gly-Ser-Val (GSV), Ser-Val-Ser (SVS), Leu-Gly-Ser (LGS), Val-Arg-Phe (VRF), Ser-Asn-Thr (SNT), Arg-Phe-Arg (RFR), Asn-Thr-Arg (NTR), Leu-Ser-Asn (LSN), Gly-Phe-Val (GFV), Phe-Val-Arg (FVR), Phe-Arg-Leu (FRL), Trp-Arg-Val (WRV), Phe-Ser-Leu (FSL), Val-Phe-Ser (VFS), Val-Ala-Trp (VAW), Ser-Leu-Phe (SLF), Arg-Val-Phe (RVF), Leu-Phe-Trp (LFW), Lys-Val-Ala (KVA), Phe-Trp-Lys (FWK), Ala-Trp-Arg (AWR), Val-His-Gly (VHG), Ser-Val-His (SVH), His-Gly-Val (HGV), Arg-Val-Cys (RVC), Arg-Pro-Gln (RPQ), Gln-Lys-Ile (QKI), Pro-Gln-Lys (PQK), Asn-Gly-Ala (NGA), Lys-Ile-Asn (KIN), Ile-Asn-Gly (ING), Gly-Arg-Pro (GRP), Gly-Ala-Arg (GAR), Ala-Arg-Val (ARV), Leu-Ser-Gly (LSG), Val-Asp-Ser (VDS), Ser-Val-Asp (SVD) exhibited high frequency, selective binding and presence in CSF and brain.

Example 10: Peptide Hits after 4 Rounds of In Vivo Selection in Rats Using CSF Sampling 924 sequencing in total (including short reads, reads only found ones and sequencing which gave no sequence). The frequency of each peptide is related to the 924 total sequencing runs.

| Sequence | Reads | Frequency (%) | AA length | SEQ. ID. NO. |
|---|---|---|---|---|
| LYVLHSRGLWGFKL | 147 | 15.9 | 14 | 1 |
| LGSVS | 137 | 14.8 | 5 | 2 |
| GFVRFRLSNTR | 115 | 12.4 | 11 | 3 |
| KVAWRVFSLFWK | 57 | 6.1 | 12 | 4 |
| SVHGV | 40 | 6.1 | 5 | 5 |
| GRPQKINGARVC | 29 | 4.3 | 12 | 6 |
| MRWFFSHASQGR | 28 | 3.1 | 12 | 7 |
| RLSSVDSDLSGC | 26 | 3.0 | 12 | 8 |
| IGTLTT | 22 | 2.8 | 6 | 9 |
| YNQSLLQGYRYW | 21 | 2.3 | 12 | 10 |
| RSTASTSYPFFF | 17 | 2.2 | 12 | 11 |
| ISNRSHKGLMVG | 16 | 1.8 | 12 | 12 |
| DAAESVLVGTVR | 15 | 1.7 | 12 | 13 |
| YAWGGGWVLQWF | 12 | 1.6 | 12 | 14 |
| YSMVFVGIKL | 10 | 1.2 | 10 | 15 |
| DVAKVS | 10 | 1.0 | 6 | 16 |
| RRPAPLIMFRMI | 9 | 1.0 | 12 | 17 |
| DPQILMGVLRSIRGFGVK | 9 | 0.9 | 19 | 18 |
| SRYSIGGNNGVT | 7 | 0.9 | 12 | 19 |
| SGSGIGLDRWRV | 7 | 0.7 | 12 | 20 |
| WGCNGTEWRGLLGIKL | 6 | 0.7 | 16 | 21 |
| HAMSC | 5 | 0.6 | 5 | 22 |
| STVVCFKGVPTG | 5 | 0.5 | 12 | 23 |
| TWLFSLG | 4 | 0.5 | 7 | 24 |
| LPGGSPGHILVC | 4 | 0.4 | 12 | 25 |
| GWIPYDGGNRAR | 4 | 0.4 | 12 | 26 |
| STMRYVGVTCL | 3 | 0.4 | 11 | 27 |
| GCASPASTSFHS | 3 | 0.3 | 12 | 28 |
| LRPRGAFQRRDFKL | 3 | 0.3 | 14 | 29 |
| ELVHA | 3 | 0.3 | 5 | 30 |
| FLIQWGA VLSRG | 2 | 0.3 | 12 | 31 |
| VRDWAYVYSTVL | 2 | 0.2 | 12 | 32 |
| TAVFSALSMLRG | 2 | 0.2 | 12 | 33 |
| AVES | 2 | 0.2 | 4 | 34 |
| RPRAQGAL | 2 | 0.2 | 8 | 35 |
| LWVSVPRARHQ | 2 | 0.2 | 12 | 36 |

Example 11

Figure 7B:
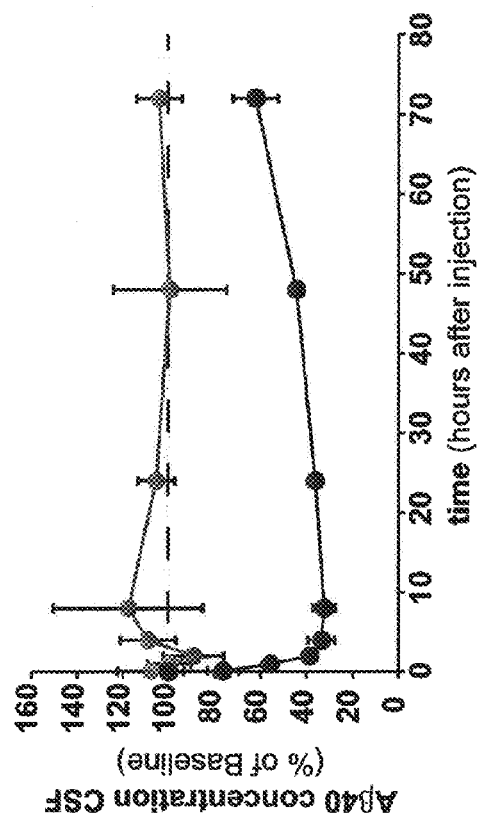
FIGS. 7A and 7B show that brain shuttle peptide with SEQ. ID. NO. 8 enhances brain BACE1 peptide inhibitory activity. A biotinylated BACE1 inhibitory peptide alone (FIG. 7B) or in combination with the likewise biotinylated brain shuttle peptide with SEQ. ID. NO. 8 (FIG. 7A) was pre-attached to streptavidin and subsequently i.v. injected (10 mg streptavidin/kg) in at least three CM cannulated rats each. BACE1 peptide inhibitor mediated Aβ40 reduction was measured by an Aβ1-40 ELISA in blood (black triangles/circles) and CSF (grey triangles/circles) at the indicated time points. For better visibility, a dashed line at 100% was drawn in the graphs.
Figure 7A:
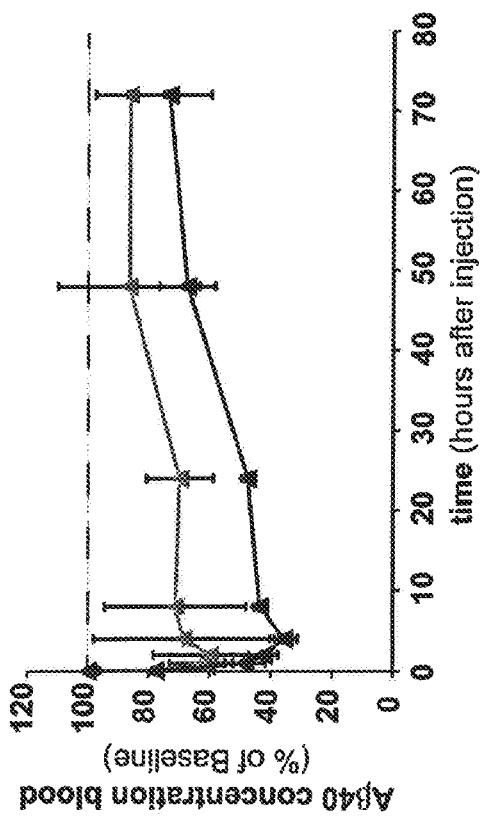

In order to investigate a peptide-mediated pharmacological effect in CNS, we performed an experiment where we mixed the brain shuttle peptide with SEQ. ID. NO. 8 with a BACE1 peptide inhibitor (both biotinylated) with Streptavidin (SA) in two different ratios. For one sample we used only the BACE1 peptide inhibitor and for the other sample we use a 1:3 ratio of the BACE1 peptide inhibitor to brain shuttle peptide with SEQ. ID. NO. 8 generating a fraction of conjugated SA complexes with a mixture of most brain shuttle peptide with SEQ. ID. NO. 8 and a single BACE1 peptide inhibitor to promote brain delivery. The two samples were intravenously injected and the level of amyloid-β peptide 40 (Abeta40) was determined in the blood and CSF. As expected, both samples had a substantial reduction in Abeta40 levels in the blood. However, only the sample with the mixture of the brain shuttle peptide with SEQ. ID. NO. 8 with the BACE1 peptide inhibitor conjugated onto SA induced a clear Abeta40 reduction in CSF (see FIG. 7A, grey line). This data shows that the brain shuttle peptide with SEQ. ID. NO. 8 is able to transport a large protein (SA) into the CNS and induce a pharmacological effect by the SA conjugated BACE1 peptide inhibitor.

Method: Functionality of the streptavidin-peptide-BACE1 inhibitor complex was assessed by Aβ(1-40) ELISA according to the manufacturer protocol (Wako, 294-64701). Briefly, CSF samples were diluted in standard diluent (1:23) and incubated overnight at 4° C. on 96-well plates coated with capture antibody BNT77. After five wash steps, HRP-conjugated BA27 antibody was added and incubated for 2 hours at 4° C., followed by five wash steps. Aβ(1-40) was detected by incubation in TMB solution for 30 minutes at room temperature. Absorbance was read out at 450 nm after stopping color development with stop solution. Plasma samples underwent solid phase extraction before Aβ(1-40) ELISA. Plasma was added to 0.2% DEA (Sigma) in 96-well plate and incubated for 30 minutes at room temperature. After washing the SPE plate (Oasis, 186000679) with 100% methanol followed by water, plasma samples were added to the SPE plate and any liquid got removed. The samples were washed (5% methanol followed by 30% methanol) and eluted in 2% NH4OH/90% Methanol. After drying the eluates at 55° C. for 99 minutes under constant N2-flow, the samples were reconstituted in standard diluent and Aβ(1-40) measured as indicated above.

REFERENCES

Arap et. al, Science, 279 377-3 80, 1998a.
Arap et al, Curr Opin Oncol, 10 560-565, 1998b.
Arap et al, Nature Med 8, 121-127, 2002.
Baichwal and Sugden, In Gene Transfer, Kucherlapati (Ed), NY, Plenum Press, 117-148, 1986.
Bakhshi et al, Cell, 41(3) 899-906, 1985. Barany and Memfield, In The Peptides, Gross and Meienhofer (Eds), Academic Press, NY, 1-284, 1979.
Breije et al, J 1-Jistochem Cytochem, 50 365-383, 2002
Brooks et al, Cell, 79 1157-1164, 1994. Brou et al, Mol Cell, 5 207-2 16, 2000.
Burg et al, Cancer Res, 582869-2874, 1999.
Carhn and Louis, In Bayes and Empirical Bayes Methods [or Data Analysis, 2' Ed, Chapman & Hall/CRC, London, U K, 2000.
Chen and Okayama, Mol Cell Biol, 7 2745-2752, 1987.
Cleary and Skiar, Proc Natl Acad Sci USA, (21) 7439-7443, 1985.
Cleary et al, J Exp Med, 164(1) 315-320, 1986.
Coffin, In Virology, Fields et al (Eds), Raven Press, NY, 1437-1500, 1990.
Coupareta, Gene, 68 1-10, 1988.

Elicein and Cheresh, Curr Opin Cell Biol, 13(5) 563-568, 2001.
Ellerby et al, Nature Med, 9 1032-1038, 1999.
Folkman, Nature Biotechnol, 15, 510, 1997.
Folkman, Nature ed, 1 27-31, 1995.
Freemark et al, Endocrinology, 143 1378-85, 2002.
Freedman, Science, 244 1275-128 1, 1989.
Gomez Foix et al, J Biol Chem, 267 25129 25134, 1992.
Goodman and Gilman's The Pharmacological Basis of Therapeutics, Hardman et al (Eds), 10111 Ed, 32 853-860, 35 891-893, 2001.
Gopal, Mol Cell Biol, 5 1188-1190, 1985.
Graham and Prevec, In Methods in Molecular Biology Gene Transfer and Expression Protocol, Murray (Ed), Humana Press, Clifton, N.J., 7 109-128, Graham and van der Eb, Virology, 52 456-467, 1973.
Graham et al, J Gen Virol, 36 59-72, 1977.
Grunhaus and Horwitz, Seminar in Virology, 3 237-252, 1992.
Harlow and Lane, Antibodies A Laboratory Manual, Cold Spring Harbor Laboratory Press, N Y, 1988.
Herrnonat and Muzycska, Proc Natl Acad Sci USA, 81 6466-6470, 1984.
Herz and Gerard, Proc Natl Acad Sci USA, 90 2812 2816, 1993.
Horwich, et al, J Virol, 64 642-650, 1990.
Johnson et al, In Peptide Turn Mimetics, Pezzuto et al (Eds), Chapman and Hail, N Y, 1993.
Jones and Shenk, Cell, 13 181-188, 1978. Kerr et al, Br J Cancer, 26(4) 23 9-257, 1972.
Koivunen et al, Methods Mol Biol, 129 3-17, 1999b.
Kowunen et al, Nature Biotechnol, 17 768-774, 1999a.
Kolonin et al, Curr Opin Chem Biol, 5 308-3 13, 2001.
Kolonin et at, Nature Med, 6 625-632, 2004.
Kolonin et al, Proc Natl Acad Sci USA, 9913055-13060, 2002.
Le Gal La Salle et al, Science, 259 988-990, 1993.
Levrero et al, Gene, 101 195-202, 1991.
Lindnereta, Am J Pathol, 159 875-883, 2001.
Mernfield, Science, 232 341-347, 1986.
Needleman et al, Journal of Molecular Biology 48 443-53, 1970.
Nicolas and Rubinstein, In Vectors A survey of molecular cloning vectors and their uses, Rodriguez and Denhardt (Eds), Stoneham Butterworth, 494-5 13, 1988.
Nicolau et al, Methods Enzymol, 149 157-176, 1987.
Paskind et al, Virology, 67 242-248, 1975.
Pasqualini and Ruoslahti, Nature, 380 364-3 66, 1996.
Pasqualini et al, Cancer Res, 60 722-727, 2000.
Pasqualini et al, In Phage Display A Laboratory Manual Barbas et al., (Eds), 221 22-24, Cold Spring Harbor Laboratory Press, N Y, 2001.
Pasqualini, J Nucl Med, 43 159-162, 1999.
Physicians' Desk Reference
Potter et al, Proc Nat Acad Sci USA, 81 7161-7165, 1984.
Racher et al, Biotechnology Techniques, 9 169-174, 1995.
Ragot et al, Nature, 361 647-650, 1993.
Rajotte and Ruoslahti, J Biol Chem, 274 11593-11598, 1999.
Rajotte et al, J Clin Invest, 102 430-437, 1998.
Remington's Pharmaceutical Sciences, 15 ed, 33 624-652, Mack Publishing Company, Easton, Pa., 1980.
Rich et al, Hum Gene Ther, 4 46 1-476, 1993.
Ridgeway, In Vectors A Survey of Molecular Cloning Vectors and Their Uses, Rodriguez et al., (Eds), Stoneham Butterworth, 467-492, 1988.
Rippe et al, Mol Cell Biol, 10689-695, 1990.
Rosenfeld et al, Cell, 68 143-155, 1992.
Rosenfeld et al, Science, 252 431-434, 1991.
Smith and Scott, Meth Enzymol, 21 228-257, 1993.
Smith and Scott, Science, 228 1315-1317, 1985.
Stewart and Young, In Solid Phase Peptide Synthesis, 2nd Ed, Pierce Chemical Co, Stratford-Perncaudet and Perncaudet, In Human Gene Transfer, Cohen-Haguenauer et al (Eds), John Libbey Euro text, France, 51-61, 1991.
Stratford-Pemcaudet et al, Hum Gene Ther, 1 24 1-256, 1990.
Tam et al, J Am Chem Soc, 1056442, 1983.
Temin, In Gene Transfer, Kucherlapati (Ed), NY, Plenum Press, 149-188, 1986.
Tsujimoto and Croce, Proc Natl Acad Sci USA, 83(14) 5214-5218, 1986.
Tsujimoto et al, Science, 228 (4706) 1440-1443, 1985.
Tur-Kaspa et al, Mol Cell Biol, 6 716-718, 1986.
Wiemers et al, Endocrinology 144 3 13-325, 2003.
Wong et al, Gene, 1087-94, 1980.
Wu and Wu, Biochemistry, 27 887-892, 1988.
Wu and Wu, J Biol Chem, 262 4429-4432, 1987.
Zunta et al, Cancer Res, 64 435-43 9, 2004.

The invention claimed is:

1. A blood brain barrier shuttle comprising a brain effector entity and a brain targeting peptide, wherein said brain targeting peptide is selected from the group consisting of SEQ. ID. NOs. 1 to 36.

2. The blood brain barrier shuttle of claim 1 comprising the brain effector entity, a linker and the brain targeting peptide wherein the linker couples the effector entity to the brain targeting peptide.

3. The blood brain barrier shuttle of claim 1, wherein the brain targeting peptide is selected from the group consisting of SEQ. ID. NOs. 1, 6 and 8.

4. The blood brain barrier shuttle of claim 1, wherein the brain effector entity is selected from the group consisting of neurological disorder drugs, neurotrophic factors, growth factors, enzymes, cytotoxic agents, antibodies directed to a brain target, monoclonal antibodies directed to a brain target, peptides directed to a brain target.

5. The blood brain barrier shuttle of claim 4, wherein the brain target is selected from the group consisting of β-secretase 1, Aβ, epidermal growth factor, epidermal growth factor receptor 2, Tau, phosphorylated Tau, apolipoprotein E4, alpha synuclein, oligomeric fragments of alpha synuclein, CD20, huntingtin, prion protein, leucine rich repeat kinase 2, parkin, presenilin 2, gamma secretase, death receptor 6, amyloid precursor protein, p75 neurotrophin receptor and caspase 6.

6. The blood brain barrier shuttle of claim 1, wherein the brain effector entity is selected from the group consisting of proteins, polypeptides and peptides.

7. The blood brain barrier shuttle of claim 1, wherein the brain effector entity comprises a full length antibody directed to a brain target.

8. The blood brain barrier shuttle of claim 7, wherein the brain effector entity is a full length IgG.

9. The blood brain barrier shuttle of claim 7, wherein the effector entity is a full length antibody directed to Aβ.

10. The blood brain barrier shuttle of claim 7, wherein the effector entity is a full length antibody directed to phosphorylated Tau.

11. The blood brain barrier shuttle of claim 7, wherein the effector entity is a full length antibody directed to alpha synuclein.

12. A pharmaceutical formulation comprising the blood brain barrier shuttle of claim 1, and a pharmaceutically acceptable carrier.

* * * * *